United States Patent
Held et al.

(10) Patent No.: US 9,382,185 B2
(45) Date of Patent: Jul. 5, 2016

(54) PROCESSES FOR CONVERTING BIOMASS-DERIVED FEEDSTOCKS TO CHEMICALS AND LIQUID FUELS

(71) Applicant: Virent, Inc, Madison, WI (US)

(72) Inventors: Andrew Held, Madison, WI (US); Elizabeth Woods, Middleton, WI (US); Randy Cortright, Madison, WI (US); Matthew Gray, Highlands Ranch, CO (US)

(73) Assignee: Virent, Inc., Madison, WI (US)

( * ) Notice: Subject to any disclaimer, the term of this patent is extended or adjusted under 35 U.S.C. 154(b) by 0 days.

(21) Appl. No.: 14/215,283

(22) Filed: Mar. 17, 2014

(65) Prior Publication Data

US 2014/0273118 A1 Sep. 18, 2014

Related U.S. Application Data

(60) Provisional application No. 61/786,788, filed on Mar. 15, 2013.

(51) Int. Cl.
| | |
|---|---|
| *C07C 51/377* | (2006.01) |
| *C07C 45/60* | (2006.01) |
| *C07C 29/132* | (2006.01) |
| *C07C 41/09* | (2006.01) |
| *C07C 45/59* | (2006.01) |
| *C10G 3/00* | (2006.01) |
| *C10L 1/02* | (2006.01) |

(52) U.S. Cl.
CPC ............ *C07C 51/377* (2013.01); *C07C 29/132* (2013.01); *C07C 41/09* (2013.01); *C07C 45/59* (2013.01); *C07C 45/60* (2013.01); *C10G 3/52* (2013.01); *C10L 1/02* (2013.01); *C10G 2300/1014* (2013.01); *C10G 2300/1018* (2013.01); *Y02P 30/20* (2015.11)

(58) Field of Classification Search
CPC ........ C07C 1/22; C07C 45/60; C07C 51/377; C07C 29/60
See application file for complete search history.

(56) References Cited

U.S. PATENT DOCUMENTS

| | | | |
|---|---|---|---|
| 3,709,979 | A | 1/1973 | Chu |
| 3,832,449 | A | 8/1974 | Rosinski |
| 4,016,245 | A | 4/1977 | Plank et al. |
| 4,076,842 | A | 2/1978 | Plank |
| 4,100,262 | A | 7/1978 | Pelrine |
| 4,107,195 | A | 8/1978 | Rollmann |
| 4,139,600 | A | 2/1979 | Rollmann et al. |
| 4,375,573 | A | 3/1983 | Young |
| 5,019,663 | A | 5/1991 | Chou et al. |
| 7,022,888 | B2 | 4/2006 | Choudhary et al. |
| 7,767,867 | B2 | 8/2010 | Cortright |
| 2011/0009614 | A1 | 1/2011 | Blommel |
| 2012/0095274 | A1* | 4/2012 | Bao ........................ B01J 23/882 585/319 |
| 2014/0242867 | A1* | 8/2014 | Jansen .................... C07G 1/00 442/181 |

OTHER PUBLICATIONS

White et al, Basic Energy Sciences Advisory Committee Subpanel Workshop Report, Opportunities for Catalysis in the 21st Century, 2002, pp. 1-47.*

* cited by examiner

*Primary Examiner* — Paul A Zucker
(74) *Attorney, Agent, or Firm* — Quarles & Brady LLP

(57) ABSTRACT

The present invention provides processes, methods, and systems for converting biomass-derived feedstocks to liquid fuels and chemicals. The method generally includes the reaction of a hydrolysate from a biomass deconstruction process with hydrogen and a catalyst to produce a reaction product comprising one of more oxygenated compounds. The process also includes reacting the reaction product with a condensation catalyst to produce $C_{4+}$ compounds useful as fuels and chemicals.

23 Claims, 7 Drawing Sheets

PROCESSES FOR CONVERTING BIOMASS-DERIVED FEEDSTOCKS TO CHEMICALS AND LIQUID FUELS

CROSS-REFERENCE TO RELATED APPLICATIONS

This application claims the benefit of U.S. provisional Application No. 61/786,788 filed on Mar. 15, 2013, which is incorporated by reference herein in its entirety.

FEDERALLY SPONSORED RESEARCH OR DEVELOPMENT

This invention was made with government support under an award provided by the U.S. Department of Energy, Award Nos. DE-EE0003044. The government has certain rights in the invention.

BACKGROUND OF THE INVENTION

Increasing cost of fossil fuel and environmental concerns have stimulated worldwide interest in developing alternatives to petroleum-based fuels, chemicals, and other products. Biomass (material derived from living or recently living biological materials) is a possible renewable alternative to petroleum-based fuels and chemicals.

Plant biomass is the most abundant source of carbohydrate in the world due to the lignocellulosic materials in its cell walls, making it a desirable source of biomass. Lignocellulosic biomass includes three major components: (1) cellulose, a primary sugar source for bioconversion processes, includes high molecular weight polymers formed of tightly linked glucose monomers; (2) hemicellulose, a secondary sugar source, includes shorter polymers formed of various sugars (e.g., xylose, mannose, glucose, galactose, etc.); and (3) lignin that includes phenylpropanoic acid moieties polymerized in a complex three dimensional structure.

Plant cell walls include up to three layers, the two most common being primary cell walls and secondary cell walls. The primary cell wall provides structure for expanding cells and is composed of major polysaccharides (cellulose, hemicellulose, and pectin) and structural proteins (i.e., glycolproteins). The cellulose microfibrils are linked via hemicellulosic tethers to form the cellulose-hemicellulose network that is embedded in the pectin matrix. The outer part of the primary cell wall is usually impregnated with cutin (e.g., omega hydroxyl acids and their derivatives) and wax, forming a permeability barrier known as the plant cuticle.

The secondary cell wall, which is produced after the cell has finished growing, contains a wide range of additional compounds including polysaccharides and lignin. The lignin interpenetrates the cellulose, hemicellulose and pectin of the primary cell wall to provide additional strength via covalent cross-linking with the hemicellulose. While the relative composition of polysaccharides varies between plants, cell type, and age, the composition of lignocellulosic biomass is roughly 40-50% cellulose, 20-25% hemicellulose, and 25-35% lignin, by weight percent.

The additional compounds, or minor components, present in both the primary and secondary walls include a variety of species (e.g., inorganic materials, color bodies, and waxes) at varying concentrations. Additional minor components may derive from material associated with the production, processing, or handling of lignocellulosic biomass, such as soil or fertilizer. The minor components can be divided into two categories: (1) extractives, non-structural biomass components including terpenoids, stilbenes, flavonoids, phenolics, aliphatics, lignans, alkanes, and proteinaceous materials; and (2) ash, inorganic components such as aluminum, barium, calcium, iron, potassium, magnesium, manganese, phosphorous, sulfur, chloride, ammonium, sulfate, sulfite, thiol, silica, copper, carbonate, phosphorous, etc.

Very few cost-effective processes exist for efficiently deconstructing biomass and converting cellulose, hemicellulose, and lignin to components better suited for producing fuels, chemicals, and other products. This is generally because each of cellulose, hemicellulose, and lignin demands distinct processing conditions, such as temperatures, pressures, solvents, catalysts, reaction times, etc., in order to effectively break apart their polymeric structures. As a result, most processes are effective for converting only specific fractions, such as cellulose and hemicellulose, leaving the remaining fraction(s) behind for additional processing, or alternative uses.

The deconstruction process can introduce new compounds into the feedstock from the degradation of the biomass components. For example, deconstruction of biomass results in the deconstruction of polysaccharides into more desirable smaller saccharides, for example mono-, di-, or trisaccharides. The deconstruction process also introduces degradation products into the feedstock. The presence of sugar degradation products like organic acids and cyclic ethers signifies a lowering of the overall yield of desirable saccharides. As a result, one would expect the presence of sugar degradation products to be undesirable, and their production should be minimized. Surprisingly, the present methods are not only tolerant of sugar degradation products, but the sugar degradation products improve the effectiveness of the process to produce desirable monooxygenates from the biomass-derived feedstock Regardless of the deconstruction process used, the resulting feedstock is likely to contain the desired oxygenated hydrocarbons (e.g. sugars) as well as sugar degradation products, extractives, ash, mineral salts, mineral acids, and other solvents used in the deconstruction. The latter components in the heterogeneous mixture can have an impact on biomass conversion efficiencies. Ash components, even at relatively low concentrations, can severely limit thermochemical, biochemical, and catalytic conversion of biomass by affecting operating temperatures, inhibiting fermentation, and poisoning catalysts. As a result, methods for purifying biomass-derived feedstocks prior to conversion and processes that are semi-tolerant to extractives and ash components are of interest. The latter could be especially important in making biomass a realistic alternative to petroleum feedstocks, as highly or completely pure feedstocks could carry additional costs, such as capital expenditures on equipment and processing systems.

SUMMARY

The invention provides methods for producing oxygenated compounds from a biomass-derived feedstock. The method generally involves providing an aqueous feedstock, catalytically reacting a portion of the aqueous feedstock with hydrogen in the presence of a catalyst at a reaction temperature and a reaction pressure to produce a reaction product.

The invention is a method for producing oxygenated compounds from a biomass-derived feedstock, the method comprising: providing an aqueous feedstock, the aqueous feedstock comprising water; greater than about 20 wt % of a plurality of first oxygenated hydrocarbons, the first oxygenated hydrocarbons selected from the group consisting of monosaccharides, disaccharides, trisaccharides, oligosaccharides, and combinations thereof; between about 1 wt % and about 40 wt % of a plurality of second oxygenated hydrocarbons, the second oxygenated hydrocarbons comprising sugar degradation products; and ash, wherein the ash comprises less than about 75 ppm sulfur and less than about 30 ppm phosphorous; and reacting a portion of the aqueous feedstock with hydrogen in the presence of a catalyst, the catalyst comprising at least one Group VIII metal, to produce a reaction product comprising one or more oxygenated compounds selected from the group consisting of an alcohol, a ketone, a cyclic ether, a carboxylic acid, an aldehyde, a diol, and a polyol.

In one embodiment, the aqueous feedstock is prepared by a biomass deconstruction method and the deconstruction method is selected from the group consisting of thermochemical biomass deconstruction, enzymatic biomass deconstruction, catalytic biomass deconstruction, and combinations thereof. In another embodiment, the aqueous feedstock is further prepared by a treatment method and the treatment method is selected from the group consisting of physical separation, chemical separation, neutralization, catalytic reaction, and combinations thereof.

In one embodiment, the aqueous feedstock may comprise greater than 30 wt %, greater than 40 wt %, or greater than 50 wt % of the first oxygenated hydrocarbons. The aqueous feedstock may also comprise greater than 2 wt %, greater than 3 wt %, greater than 4 wt %, or greater than wt % of the second oxygenated hydrocarbons. The aqueous feedstock may also comprise less than 35 wt %, less than 30 wt %, less than 25 wt %, or less than 20 wt % of the second oxygenated hydrocarbons. The aqueous feedstock may also comprise between 1 wt % and 25 wt % furfurals. The aqueous feedstock may also comprise the second oxygenated hydrocarbons having greater than 2 wt %, greater than 3 wt %, greater than 4 wt %, or greater than 5 wt % furfurals. The aqueous feedstock may also comprise the second oxygenated hydrocarbons having less than 20 wt %, less than 15 wt %, or less than 10 wt % furfurals.

In one embodiment, the aqueous feedstock may comprise less than 70 ppm, less than 60 ppm, or less than 50 ppm sulfur. The aqueous feedstock may also comprise less than 25 ppm phosphorus, less than 20 ppm, less than 15 ppm, or less than 10 ppm phosphorus.

In one embodiment, the aqueous feedstock further comprises extractives, lignin, lignin derivatives, solids, or combinations thereof.

In one embodiment, the catalyst further comprises a metal selected from Group IVB, Group VB, Group VIB, Group VIIB, Group IB, or the Lanthanides.

In one embodiment, the invention further comprises reacting a portion of the reaction product with a condensation catalyst at a condensation temperature and a condensation pressure to produce $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, and a fused aryl. The $C_{4+}$ compounds may be distilled to provide a composition selected from the group consisting of an aromatic fraction, a gasoline fraction, a kerosene fraction, and a diesel fraction. The $C_{4+}$ compounds may also comprise one or more aryls selected from the group consisting of benzene, toluene, xylene, para-xylene, meta-xylene, and ortho-xylene.

Another aspect of the invention provides for producing oxygenated compounds from a biomass-derived feedstock, the method comprising: deconstructing biomass with a deconstruction method to produce an intermediate feedstock, the intermediate feedstock comprising oxygenated hydrocarbons, ash, extractives, lignin, lignin derivatives, and solids; treating the intermediate feedstock with a treatment method to produce an aqueous feedstock, the aqueous feedstock comprising: water; greater than 20 wt % of a plurality of first oxygenated hydrocarbons, the first oxygenated hydrocarbons selected from the group consisting of monosaccharides, disaccharides, trisaccharides, oligosaccharides, and combinations thereof; between 1 wt % and 40 wt % of a plurality of second oxygenated hydrocarbons, the second oxygenated hydrocarbons comprising sugar degradation products; and ash, wherein the ash comprises less than 75 ppm sulfur and less than 30 ppm phosphorous; and reacting a portion of the aqueous feedstock with hydrogen in the presence of a catalyst, the catalyst comprising at least one Group VIII metal, to produce one or more oxygenated compounds selected from the group consisting of an alcohol, a ketone, a cyclic ether, a carboxylic acid, an aldehyde, a diol, and a polyol.

In one embodiment, the deconstruction method is selected from the group consisting of thermochemical biomass deconstruction, enzymatic biomass deconstruction, catalytic biomass deconstruction, and combinations thereof. In another embodiment, the treatment method is selected from the group consisting of physical separation, chemical separation, neutralization, catalytic reaction, and combinations thereof. In one embodiment, the invention further comprises reacting a portion of the oxygenated compounds with a condensation catalyst at a condensation temperature and a condensation pressure to produce $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, and a fused aryl.

BRIEF DESCRIPTION OF THE DRAWINGS

FIG. 1A is an exemplary flow diagram for converting oxygenated hydrocarbons to oxygenated compounds. FIG. 1B is an exemplary flow diagram for converting oxygenated hydrocarbons to oxygenated compounds including an optional recycle stream.

DESCRIPTION OF THE INVENTION

Processes, methods, and systems for converting biomass-derived feedstocks to liquid fuels and chemicals are described herein. The method generally consists of reacting hydrogen and an aqueous feedstock comprising water, oxygenated hydrocarbons, and ash with a catalyst to produce a reaction product comprising one of more oxygenated compounds. The method may optionally comprise reacting the reaction product with a condensation catalyst to produce $C_{4+}$ compounds.

The biomass-derived feedstocks of the present invention comprise a plurality of first oxygenated hydrocarbons and a plurality of second oxygenated hydrocarbons. The first oxygenated hydrocarbons may include monosaccharides, disaccharides, trisaccharides, oligosaccharides, and combinations thereof, at amounts greater than 20 wt % of the feedstock. The first oxygenated hydrocarbon may also originate from smaller sugars such as monosaccharides or disaccharides like glucose or sucrose or may be a derivative of a larger polysaccharide like starch, cellulose, or hemicellulose.

The second oxygenated hydrocarbons are generally sugar degradation products, and are present at amounts between 1 wt % and 40 wt % of the feedstock. The process of deconstructing biomass may naturally degrade some of the sugars that would otherwise be available as a first oxygenated hydrocarbon. Despite the depletion of available first oxygenated hydrocarbons, the sugar degradation products surprisingly enhance the overall conversion process of converting oxygenated hydrocarbon to oxygenated compounds.

A third component of the biomass-derived feedstock is ash. Although ash has been known to negatively impact catalyst performance, the methods, systems, catalysts, and reactors of the present invention can tolerate the presence of ash. In certain cases, the feedstock may have a high wt % of ash without a significant decrease in overall catalyst performance.

Figure 1A:
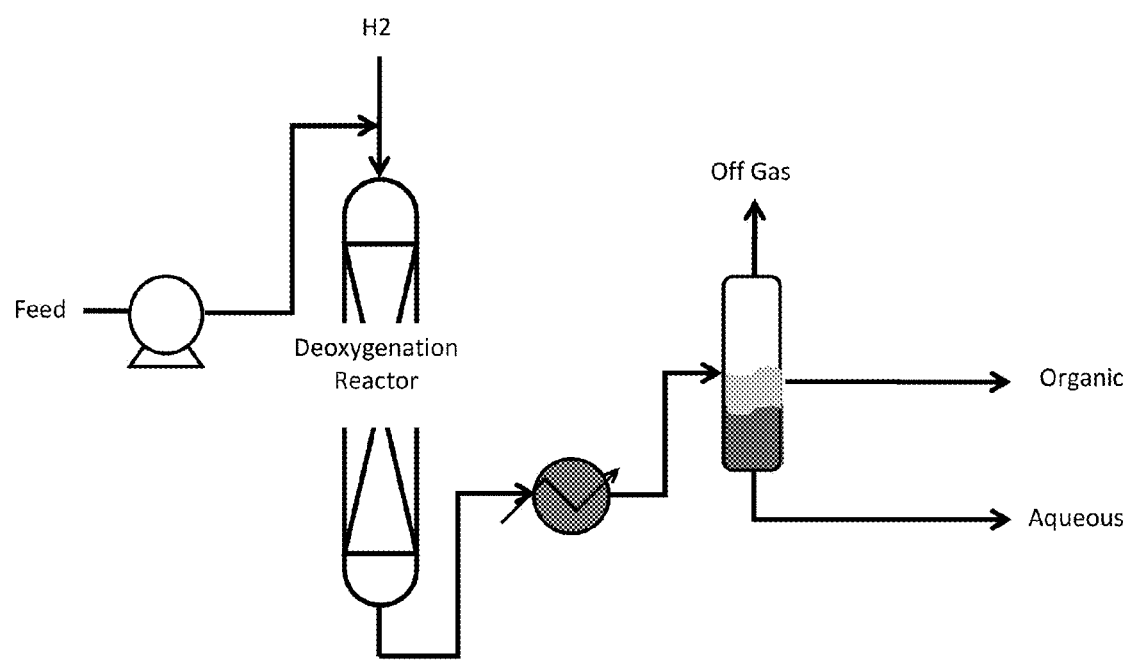
FIGS. 1A and 1B are process flow diagrams of a first and second embodiment of a process for converting biomass-derived feedstocks to oxygenated compounds.
Figure 1B:
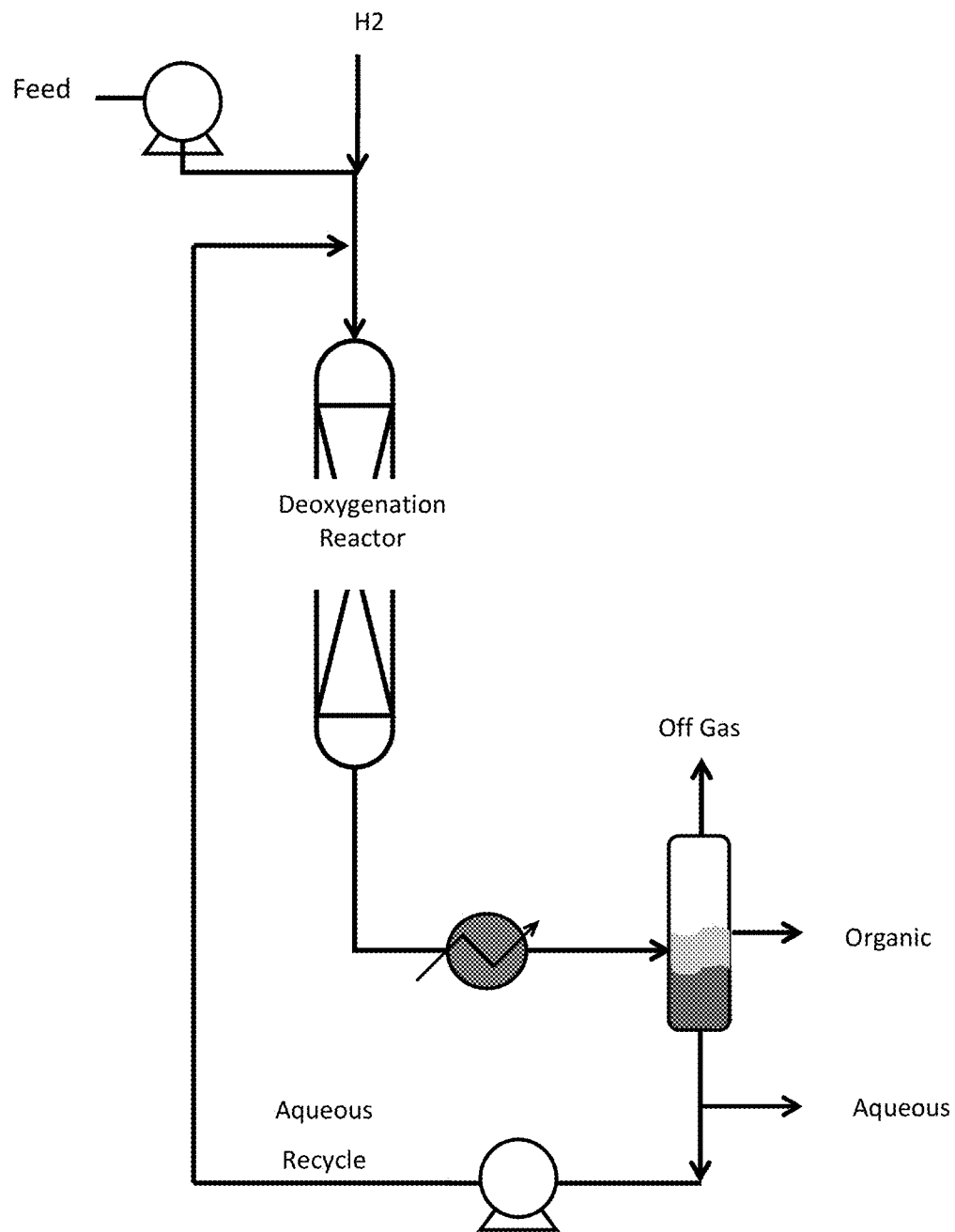

An overview of the reaction system is provided. FIGS. 1A and 1B disclose exemplary methods for producing oxygenated compounds, such as $C_{2+}O_{1+}$ alcohols, ketones, cyclic ethers, esters, carboxylic acids, aldehydes, diols, triols, and mixtures thereof. The disclosed methods include catalytically reacting $C_{2+}O_{2+}$ oxygenated hydrocarbons (e.g., sugars, sugar alcohols, sugar degradation products, etc.) with hydrogen in the presence of a catalyst. The temperature and pressure conditions for the reaction may be varied depending on the feedstock composition and the desired products (e.g., oxygenated compounds or hydrocarbons).

Figure 3:
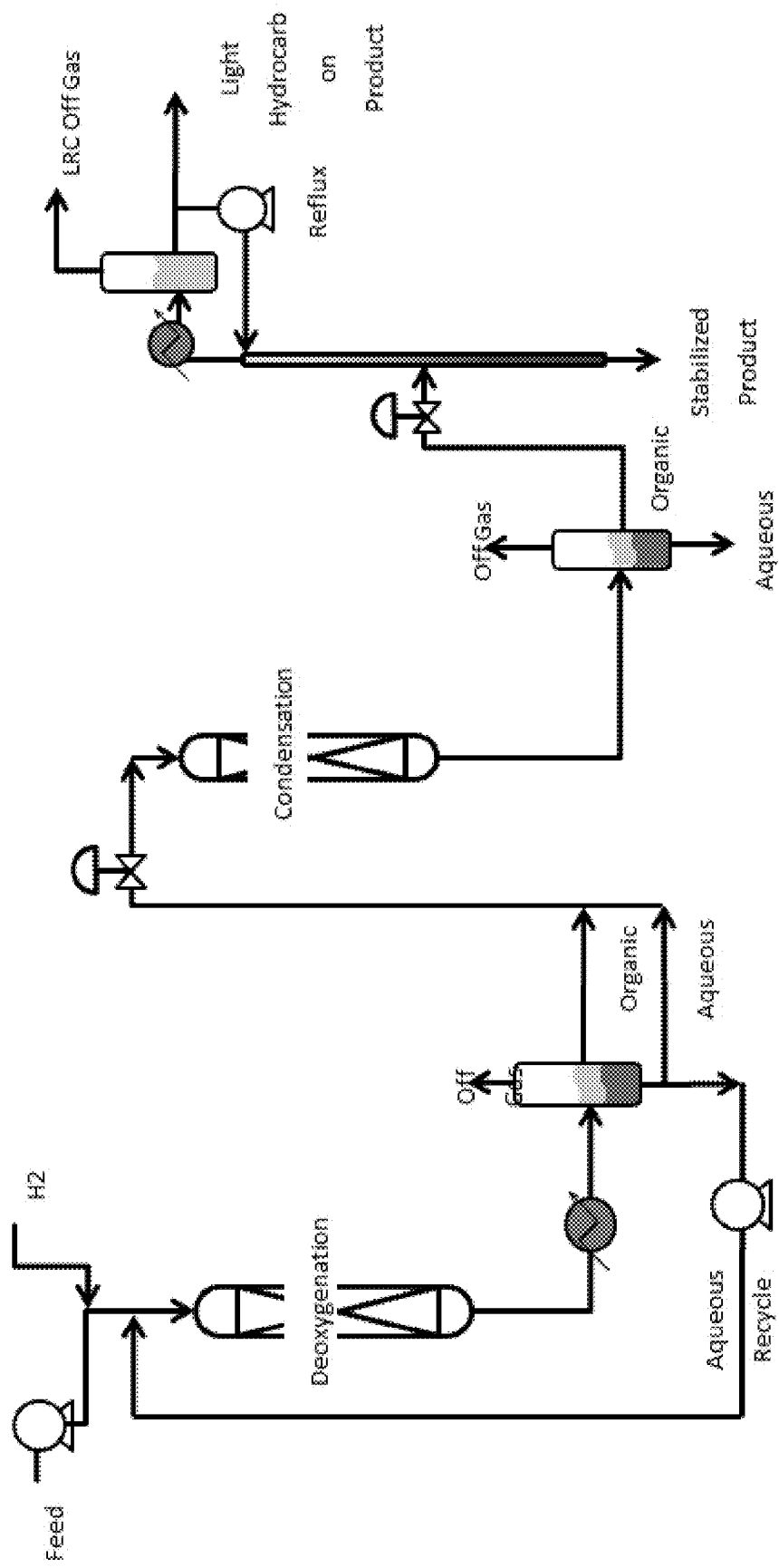
FIG. 3 is a flow diagram of an embodiment of a process for producing liquid fuels and chemicals from biomass-derived feedstocks that includes a deoxygenation reactor, a condensation reactor, and a recycle stream.

FIG. 3 discloses an exemplary method for producing $C_{4+}$ compounds, such as $C_{4+}$ alcohols, $C_{4+}$ ketones, $C_{4+}$ alkanes, $C_{4+}$ alkenes, $C_{4+}$ cycloalkanes, $C_{4+}$ cycloalkenes, an aryl, a fused aryl, an oxygenated aryl, an oxygenated fused aryl, and mixtures thereof. The disclosed method includes catalytically reacting oxygenated hydrocarbons with hydrogen in the presence of a catalyst under conditions sufficient to produce oxygenated compounds. An oxygenated compound is then catalytically reacted with another oxygenated hydrocarbon or other functionalized hydrocarbon in the presence of a condensation catalyst under conditions sufficient to produce $C_{4+}$ compounds.

Further description and possible variations of the invention for the methods, catalysts, products, and reactor systems is provided below.

Feedstocks

Feedstocks comprising oxygenated hydrocarbons useful in the process may originate from any source, but are generally derived from biomass. The feedstocks may be pure materials, purified mixtures, or raw materials such as sugars and starches derived from the processing of corn, sugarcane, beet sugars, pine, rice, wheat, algae, or energy crops. Some applicable feedstocks are also commercially available and may be obtained as by-products from other processes, such as glycerol from biodiesel fuel production. The feedstocks can also be intermediates formed as part of a larger process or in the same process, such as sugar alcohols produced in the initial stage of sugar hydrogenation.

As used herein the terms "lignocellulosic biomass" and "biomass" refer to, without limitation, organic materials produced by plants (e.g., wood, leaves, roots, seeds, stalks, etc.), and microbial and animal metabolic wastes. Common biomass sources include: (1) agricultural residues, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; (4) energy crops, such as poplars, willows, switch grass, pine, miscanthus, sorghum, alfalfa, prairie bluestream, corn, soybean, and the like; (5) residual solids from industrial processes, such as lignin from pulping processes, acid hydrolysis, or enzymatic hydrolysis; and (6) algae-derived biomass, including carbohydrates and lipids from microalgae (e.g., *Botryococcus braunii, Chlorella, Dunaliell tertiolecta, Gracilaria, Pleurochyrsis carterae*, and *Sargassum*) and macroalgae (e.g., seaweed). The term also refers to the primary building blocks of the above, namely, lignin, cellulose, hemicellulose, derivatives thereof, and carbohydrates, such as saccharides of any size (i.e. monosaccharides, disaccharides, trisaccharides, oligosaccharides, or polysaccharides), sugars, and starches, among others. A person of ordinary skill in the art will appreciate that different terms can be used to refer to the same molecules depending on the context. For example, the term "sugar" can include simple sugars, e.g. monosaccharides like glucose or fructose, or complex sugars, e.g. disaccharides like sucrose or maltose or even larger molecules.

The term "oxygenated hydrocarbon" refers to any molecule which can be represented as $C_{2+}O_{2+}$. Examples include without limitation, lignin, cellulose, hemicellulose, derivatives thereof, carbohydrates (e.g., monosaccharides, disaccharides, oligosaccharides, polysaccharides, and starches), sugars (e.g., glucose, sucrose, xylose, etc.), sugar alcohols (e.g., diols, triols, and polyols), and sugar degradation products (e.g., hydroxymethylfurfural (HMF), levulinic acid, formic acid, and furfural).

The term "oxygenated compound" refers to a molecule having two or more carbon atoms and one or more oxygen atoms, which can herein be represented as $C_{2+}O_{1+}$. The term "monooxygenates" refers to a hydrocarbon molecule containing two or more carbon atoms and one oxygen atom. The term "dioxygenates" refers to a hydrocarbon molecule containing two or more carbon atoms and two oxygen atoms. The term "polyoxygenates" refers to a hydrocarbon molecule containing two or more carbon atoms and three or more oxygen atoms.

The feedstock of the present invention comprises: (i) water; (ii) greater than 20 wt % of a plurality of first oxygenated hydrocarbons, the first oxygenated hydrocarbons selected from the group consisting of monosaccharides, disaccharides, trisaccharides, oligosaccharides, and combinations thereof; (iii) between 1 wt % and 40 wt % of a plurality of second oxygenated hydrocarbons, the second oxygenated hydrocarbons comprising sugar degradation products; and (iv) ash.

The first oxygenated hydrocarbons are selected from the group consisting of monosaccharides, disaccharides, trisaccharides, oligosaccharides, and combinations thereof. In certain cases, first oxygenated hydrocarbons are monosaccharides and disaccharides. The first oxygenated hydrocarbons may be derived from biomass, particularly cellulose or hemicellulose. Monosaccharides include, without limitation, aldotetroses, ketotetroses, aldopentoses, ketopentoses, aldohexoses, and ketohexoses. Examples of monosaccharides include without limitation erythrose, threose, erythrulose, arabinose, lyxose, ribose, xylose, ribulose, xylulose, glucose, mannose, galactose, allose, altrose, gulose, idose, talose, psicose, fructose, sorbose, tagatose, or rhamnose. Disaccharides include any combination of two monosaccharides, including, without limitation, sucrose, lactulose, lactose, maltose, trehalose, or cellobiose. Trisaccharides include any combination to three monosaccharides. Oligosaccharides include any combination of four to 20 monosaccharides, and in certain cases, any combination of four to 10 monosaccharides. The feedstock comprises a plurality of first oxygenated hydrocarbons at amounts greater than 20 wt % of the feedstock. In some embodiments, the first oxygenated hydrocarbons may be greater than 25 wt %, greater than 30 wt %, greater than 35 wt %, greater than 40 wt %, greater than 45 wt %, greater than 50 wt %, greater than 55 wt %, or greater than 60 wt %, of the feedstock.

The second oxygenated hydrocarbons comprise sugar degradation products. The sugar degradation products may be derived from biomass, particularly cellulose or hemicellulose. The sugar degradation product may be any dehydration product of a monosaccharide, disaccharide, trisaccharide, oligosaccharide, or combinations thereof. Common sugar degradation products are heterocyclic compounds, organic acids, sugar alcohols, ketones, aldehydes, as well as other products. Heterocyclic compounds may include cyclic ether or lactone moieties. Examples of heterocyclic compounds include, without limitation, furan, furfural, or hydroxymethylfurfural, hydroxymethylfuranone, levoglucosan, sorbitan, isomaltol, and humins. Examples of organic acids include, without limitation, levulinic acid, formic acid, pyruvic acid, gluconic acid, glyceric acid, succinic acid, and lactic acid. Examples of sugar alcohols include, without limitation glycol and glycerol. Other product might include, without limitation, compounds such as glyceraldehyde and glycoaldehyde. The second oxygenated hydrocarbon may be present at any wt % between 1 wt % and 40 wt %, including greater than 2 wt %, greater than 3 wt %, greater than 4 wt %, greater than 5 wt %, greater than 6 wt %, greater than 7 wt %, greater than 8 wt %, greater than 9 wt %, greater than 10 wt %, greater than 15 wt %, greater than 20 wt %, greater than 25 wt %, greater than 30 wt %, greater than 35 wt %, and less than 35 wt %, less than 30 wt %, less than 25 wt %, less than 20 wt %, less than 15 wt %, less than 10 wt %, less than 9 wt %, less than 8 wt %, less than 7 wt %, less than 6 wt %, less than 5 wt %, less than 4 wt %, less than 3 wt %, less than 2 wt %, or any wt % between any interval thereof.

The feedstock may include one or more additional oxygenated hydrocarbons having two or more carbon atoms and two or more oxygen atoms, i.e. $C_{2+}O_{2+}$. The oxygenated hydrocarbons may have an oxygen-to-carbon ratio of between about 0.5:1 to about 1:1.2. In certain cases, the oxygenated hydrocarbon has 3 to 12 carbon atoms or, and in other cases, 3 to 6 carbon atoms, but oxygenated hydrocarbon having more than 12 carbon atoms are capable of being used in the present invention. In some embodiments, the additional oxygenated hydrocarbons comprise greater than 1 wt %, greater than 2 wt %, greater than 3 wt %, greater than 4 wt %, greater than 5 wt %, greater than 6 wt %, greater than 7 wt %, greater than 8 wt %, greater than 9 wt %, greater than 10 wt %, greater than 15 wt %, greater than 20 wt %, greater than 25 wt %, greater than 30 wt %, greater than 35 wt %, greater than 40 wt %, or any wt % between any interval thereof of the feedstock.

In one embodiment, the feedstock may include sugar alcohols. The sugar alcohols may be derived from biomass either directly as a sugar degradation product or indirectly. The feedstock containing a first oxygenated hydrocarbon may be hydrogenated to convert part or substantially all of the first oxygenated hydrocarbon into a sugar alcohol (i.e. greater than 50%, greater than 60%, greater than 70%, greater than 80%, greater than 90%, greater than 95%, or any percentage between any interval thereof). When part of the first oxygenated hydrocarbon is hydrogenated to form a sugar alcohol, the feedstock may further comprise a third oxygenated hydrocarbon comprising a sugar alcohol. Method for forming sugar alcohols from the first oxygenated hydrocarbon are known (see e.g. U.S. patent application Ser. No. 12/827,827, the disclosure of which is incorporated herein by reference). In some embodiments, the sugar alcohols comprise greater than 1 wt %, greater than 2 wt %, greater than 3 wt %, greater than 4 wt %, greater than 5 wt %, greater than 6 wt %, greater than 7 wt %, greater than 8 wt %, greater than 9 wt %, greater than 10 wt %, greater than 15 wt %, greater than 20 wt %, greater than 25 wt %, greater than 30 wt %, greater than 35 wt %, greater than 40 wt %, or any wt % between any interval thereof.

In one embodiment, the feedstock may include oxygenated hydrocarbons solvated by a solvent. Non-limiting examples of solvents include: organic solvents, such as ionic liquids, acetone, ethanol, 4-methyl-2-pentanone, and other oxygenated hydrocarbons; dilute acids, such as acetic acid, oxalic acid, hydrofluoric acid; bioreforming solvents; and water. The solvents may be from external sources, recycled, or generated in-situ, such as in-situ generated oxygenated compounds (e.g. $C_{2+}O_{2+}$ oxygenated hydrocarbons). In some embodiments, the solvent may comprise greater than 1 wt %, greater than 2 wt %, greater than 3 wt %, greater than 4 wt %, greater than 5 wt %, greater than 6 wt %, greater than 7 wt %, greater than 8 wt %, greater than 9 wt %, greater than 10 wt %, greater than 15 wt %, greater than 20 wt %, greater than 25 wt %, greater than 30 wt %, greater than 35 wt %, greater than 40 wt %, or any wt % between any interval thereof of the feedstock.

In one embodiment, the feedstock may include lignin or lignin derivatives. Lignin derivatives include without limitation monomers, dimers, trimers, oligomers, and combinations thereof of phenylpropanoids that originate from lignin. Exemplary phenylpropanoids include paracoumaryl alcohol, coniferyl alcohol, and sinapyl alcohol. Lignin derivatives also include without limitation phenols, methoxyphenols, dimethoxyphenols that originate from lignin. Phenols, methoxyphenols, and dimethoxyphenols may be substituted with an alkyl moiety, alkenyl moiety, hydroxyl moiety, carbonyl moiety, or combinations thereof. Examples include without limitation phenol, 4-methyl-phenol, 4-ethyl-phenol, 4-propal2-methoxy-phenol, 4-ethyl-phenol, 4-ethyl-2-methoxy-phenol, 4-propyl-phenol, 4-ethyl-2-methoxy-phenol, 2,6-dimethoxy-phenol, 2-methoxy-4-propyl-phenol, 2-methoxy-3-(2-propenyl)-phenol, 1-(2,5-dimethoxyphenyl)-propanol, 2,6-dimethoxy-4-(2-propenyl)-phenol, and combinations thereof. In some embodiments, the lignin or lignin derivatives may comprises greater than 0.1 wt %, greater than 0.2 wt %, greater than 0.3 wt %, 0.4 wt %, greater than 0.5 wt %, greater than 0.6 wt %, greater than 0.7 wt %, greater than 0.8 wt %, greater than 0.9 wt %, greater than 1.0 wt %, greater than 1.5 wt %, greater than 2.0 wt %, greater than 2.5 wt %, greater than 3.0 wt %, greater than 3.5 wt %, greater than 4.0 wt %, greater than 4.5 wt %, greater than 5.0 wt %, or any wt % between any interval thereof wt % of an aqueous feedstock.

Chemical conversion processes (e.g., bioreforming) can be used to convert a wide range of compounds typically found in biomass-derived feedstocks, including pentoses and hexoses, monomers and oligomers, and high concentrations of heterocyclic compounds, to desirable oxygenated intermediates. In addition to the conventional sugars, chemical conversion methods can be used to convert some extractives (e.g., fatty acids and phenols) and hydrolysis byproducts (e.g., non-structural sugars, sugar alcohols, organic acids, etc.) and alcohols. However, catalysts used in chemical conversion processes can be sensitive to the inorganic profile of the heterogeneous carbohydrate feedstock. Therefore, providing a feedstock having a reduced ash component concentration, like those shown in Table 2, may provide improved catalyst lifetime, product yields, and product distributions.

The ash comprises inorganic materials. Examples include, without limitation, Al, B, Ba, Ca, Cu, Fe, K, Mg, Mn, Na, P, or S, all of which are found naturally in biomass at various amounts. For the feedstock, the total ash content should be less than 1 wt % of the feedstock. In certain embodiments, the total ash content is less than 0.5 wt %, less than 0.45 wt %, less than 0.4 wt %, less than 0.35 wt %, less than 0.3 wt %, less than 0.25 wt %, or less than 0.2 wt %. Two elements having a particularly large effect on catalyst performance are sulfur and phosphorus. The sulfur concentration may be below 75 ppm and, in certain cases, below 70 ppm, below 65 ppm, below 60 ppm, below 50 ppm, below 45 ppm, below 40 ppm, below 35 ppm, below 30 ppm, below 25 ppm, below 20 ppm, below 15 ppm, below 10 ppm, below 5 ppm, or below any ppm between any interval thereof. The phosphorus concentration may be below 30 ppm and, in certain cases, below 25 ppm, below 20 ppm, below 15 ppm, below 10 ppm, below 5 ppm, or below any ppm between any interval thereof.

Production of Feedstocks

Processes for the deconstruction of biomass include, without limitation: (1) thermochemical treatments such as water hydrolysis, acid hydrolysis, alkaline hydrolysis, and/or organosolv pulping; (2) pyrolysis, (3) enzymatic hydrolysis, or (4) catalytic biomass deconstruction. The processes may be used alone or in combination.

In water hydrolysis, the biomass is contacted with water at temperatures and pressures suitable to hydrolyze cellulose and hemicellulose to their monomeric, dimeric, trimeric, or oligomeric components. For cellulose, this includes glucose, while hemicellulose is hydrolyzed to provide, for example, xylose, galactose, mannose, arabinose, and acetic acid. Hemicellulose is more susceptible to deconstruction by water hydrolysis, so effectively deconstructing the cellulose generally requires high temperatures. However, the temperatures needed to deconstruct the biomass will also lead to sugar degradation products of the liberated sugars. Once complete, the resulting slurry contains residual or unreacted fiber from lignin, and an aqueous solution of the desired sugars and other hydrolysate products including sugar alcohols and sugar degradation products.

In acid hydrolysis, the biomass is contacted with a mineral acid (e.g., sulfuric acid, hydrochloric acid, or phosphoric acid) in the presence of steam to hydrolyze the cellulose and hemicellulose to their monomeric, dimeric, trimeric, and oligomeric components. For cellulose, this includes glucose, while hemicellulose is hydrolyzed to provide, for example, xylose, galactose, mannose, arabinose, and acetic acid. Sulfuric acid, hydrochloric acid, and phosphoric acid are the three most common mineral acids used for this process. Once complete, the resulting slurry contains the mineral acid, as well as residual or unreacted fiber from lignin, and an aqueous solution of the desired sugars and other hydrolysate products, including sugar alcohols, sugar degradation products, phenolics, aromatics, and hydrocarbons. Exemplary hydrolysate products include organic acids (e.g., acetic acid, formic acid, propionic acid, malic acid, citric acid, oxalic acid, lactic acid, butyric acid, valeric acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, hexanoic acid, heptanoic acid, etc.), phenols (e.g., 4-ethyl phenol, 4-ethyl-2-methoxy phenol, 2-methoxy-4-propyl phenol, vanillin, 4-propyl syringol, etc.), cresols, furfural, hydroxymethylfurfural, levulinic acid, formic acid, vitamin E, steroids, long chain hydrocarbons, long chain fatty acids, stilbenoids, flavonoids, terpenoids, aliphatics, lignans, and proteinaceous material.

In alkaline hydrolysis, an aqueous solution of strong base (typically $OH^-$) is contacted with the biomass to break-down its cellular components. Typically the base is particularly well suited to deconstruct the lignin, but can also deconstruct the hemicellulose and cellulose components. It is difficult, however, to get a high yield of sugars because the alkalis readily degrade the mono- and disaccharides. The hemicellulose is hydrolyzed by the base to yield xylose, galactose, mannose, arabinose, and acetic acid. Sugar degradation products like organic acids and heterocyclic compounds are also readily formed in the process. Other hydrolysate products are formed as well, including, without limitation, phenolics, aromatics, and hydrocarbons.

In organosolv pulping, an organic solvent is contacted with the biomass to deconstruct the cellular components. Typically the organic solvents readily deconstruct the hemicellulose and lignin fractions, but cellulose often may be recalcitrant to the organic solvent. The hemicellulose is hydrolyzed by the solvents to yield xylose, galactose, mannose, arabinose, and acetic acid. Sugar degradation products, like organic acids or heterocyclic compounds, are also readily formed in the process. A variety of different solvents are effective to the process including, without limitation, alcohols (e.g. methanol and ethanol), diols (e.g. ethylene glycol), triols (e.g. glycerol), ethers (e.g. furfurals), ketones, and phenols. Other hydrolysate products are formed as well, including, without limitation, phenolics, aromatics, and hydrocarbons.

In pyrolysis, the biomass is deconstructed at elevated temperatures in the absence of oxygen. In certain cases, catalyst may also be present. The resulting bio-oil product is a complex mixture of derivatives of the biomass components and sugar degradation products like organic acids and heterocyclic compounds, phenolics, aromatics, and hydrocarbons. In addition, there is an aqueous phase product that is also produced that contains water-soluble products, including water-soluble sugar degradation products such as alcohols, diols, ketones, aldehydes, organic acids, as well as others.

Enzymatic hydrolysis typically involves a thermochemical pretreatment followed by hydrolysis with cellulose enzymes. The thermochemical pretreatment is used to increase the surface area of the cellulose material to allow enzyme penetration. When compared to acid hydrolysis alone, the thermochemical pretreatment steps are generally milder (e.g., lower mineral acid concentrations, shorter treatment times, etc.). After acid pretreatment, base is added to the solution to raise the pH to a range in which the enzyme is active and, in the process, the mineral acid is converted into a mineral salt. Similar to the acid hydrolysis process, the hemicellulose is hydrolyzed by the mineral acid to xylose, galactose, mannose, arabinose, and acetic acid. The cellulose is hydrolyzed by the enzymes to glucose. Other hydrolysate products are formed as well, including, without limitation, sugar degradation products, phenolics, aromatics, and hydrocarbons.

Catalytic biomass deconstruction involves the use of a heterogeneous catalyst to hydrolyze the cellulose, hemicellulose and, in some instances, the lignin to water-soluble oxygenated hydrocarbons. The oxygenated hydrocarbons include carbohydrates, starches, polysaccharides, disaccharides, monosaccharides, sugars (including glucose, xylose, galactose, mannose, arabinose), sugar degradation products (e.g., hydroxymethylfurfural (HMF), levulinic acid, formic acid, and furfural), sugar alcohols, alditols, polyols, diols, alcohols, ketones, cyclic ethers, esters, carboxylic acids, aldehydes, phenols, cresols and other oxygenated hydrocarbon species.

In addition to the oxygenated hydrocarbons produced by any of the deconstruction methods, the feedstock further includes lignin, one or more extractives, one or more ash components, or one or more organic species (e.g., lignin derivatives). Extractives include terpenoids, stilbenes, flavonoids, phenolics, aliphatics, lignans, alkanes, proteinaceous materials, and other inorganic products. Ash components may include inorganic materials, such as Al, Ba, Ca, Fe, K, Mg, Mn, P, S, Si, and Zn, whether alone or in combination. The ash components for five exemplary feedstocks are disclosed in Table 1. Other organic species include 4-ethyl phenol, 4-ethyl-2-methoxy phenol, 2-methoxy-4-propyl phenol, vanillin, 4-propyl syringol, vitamin E, steroids, long chain hydrocarbons, long chain fatty acids, stilbenoids, etc.

Methods for treating the hydrolysate to reduce ash components, extractives, neutralize hydrolysis media, etc., include physical and chemical separations, such as filtration, ion exchange chromatography, size exchange chromatography, liquid-liquid extraction, solvent extraction, distillation, etc. Additional methods for treating the hydrolysate stream will be known to those skilled in the art.

Production of Oxygenated Compounds

The term "bioreforming" refers to, without limitation, processes for catalytically converting biomass and other carbohydrates to lower molecular weight hydrocarbons and oxygenated compounds, such as alcohols, ketones, cyclic ethers, esters, carboxylic acids, aldehydes, dioxygenates, and other polyoxygenated hydrocarbons, using aqueous phase reforming, hydrogenation, hydrogenolysis, hydrodeoxygenation and/or other conversion processes involving the use of heterogeneous catalysts. Bioreforming also includes the further catalytic conversion of such lower molecular weight oxygenated compounds to $C_{4+}$ compounds. The oxygenated compounds are prepared by reacting hydrogen with an aqueous feedstock solution containing water and the oxygenated hydrocarbons over a deoxygenation catalyst containing one or more metals selected from Group VIII, Group IVB, Group VB, Group VIB, Group VIIB, Group IB, and Group IIIB. The APR and deoxygenation catalysts may comprise one or more of Cr, Mo, W, Mn, Fe, Co, Ni, Cu, Mo, Ru, Rh, Pd, Ag, W, Re, Os, Ir, Pt, Au, Ti, Zr, Hf, V, Nb, Ta, La, and Ce, alloys thereof, and mixtures thereof. Exemplary deoxygenation catalysts include Pt, NiSn, PtRe, and PtRuSn, PdAg, PdMoSn, respectively. Various deoxygenation methods, processes, and techniques are described above, all of which are incorporated herein by reference.

The hydrogen may be generated in-situ using aqueous phase reforming (in-situ-generated $H_2$ or APR $H_2$), or a combination of APR $H_2$, external $H_2$ or recycled $H_2$, or just simply external $H_2$ or recycled $H_2$. The term "external $H_2$" refers to hydrogen that does not originate from the feedstock solution, but is added to the reactor system from an external source. The term "recycled $H_2$" refers to unconsumed hydrogen, which is collected and then recycled back into the reactor system for further use. External $H_2$ and recycled $H_2$ may also be referred to collectively or individually as "supplemental $H_2$." In general, supplemental $H_2$ may be added for purposes of supplementing the APR hydrogen, or to increase the reaction pressure within the system, or to increase the molar ratio of hydrogen to carbon and/or oxygen in order to enhance the production yield of certain reaction product types, such as diols, ketones, cyclic ethers, and alcohols.

The deoxygenation catalysts may be self-supporting (i.e., the catalyst does not need another material to serve as a support), or the catalyst may be adhered to a support. Such supports include, without limitation, nitride, carbon, silica, alumina, zirconia, titania, vanadia, ceria, boron nitride, heteropolyacid, kieselguhr, hydroxyapatite, zinc oxide, chromia, zeolites, tungstated zirconia, titania zirconia, sulfated zirconia, phosphated zirconia, acidic alumina, silica-alumina, sulfated alumina, iron aluminate, phosphated alumina, theta alumina, niobia, niobia phosphate, oxides of the foregoing, and mixtures thereof. Nanoporous supports such as zeolites, carbon nanotubes, or carbon fullerene may also be used.

In one embodiment, the catalyst support is zirconia. The zirconia may be produced via precipitation of zirconium hydroxide from zirconium salts, through sol-gel processing, or any other method. The zirconia may be present in a crystalline form achieved through calcination of the precursor material at temperatures exceeding 400° C., and may include both tetragonal and monoclinic crystalline phases. A modifying agent may be added to improve the textural or catalytic properties of the zirconia. Such modifying agents include, without limitation, sulfate, tungstenate, phosphate, titania, silica, and oxides of Group IIIB metals, especially Ce, La, or Y.

In another embodiment, the support is tungstated zirconia. The tungstated zirconia may be produced via impregnation of zirconium hydroxide with an aqueous solution containing a tungsten salt, precipitation from zirconium and tungsten salts through sol-gel processing, or any other method. The tungstated zirconia may be present in a mixed oxide crystalline form achieved through calcination of the precursor material at temperatures exceeding 400° C., or temperatures exceeding 600° C., and may include both tetragonal and monoclinic crystalline zirconia phases as well as polytungsten oxide clusters present on the catalyst support surface. A modifying agent may be added to improve the textural or catalytic properties of the tungstated zirconia. Such modifying agents include, without limitation, tungstenate, sulfate, phosphate, titania, silica, and oxides of Group IIIB metals (e.g., Ce, La, or Y).

In another embodiment the catalyst support is tungsten oxide. Tungsten oxide may be prepared via precipitation from a tungsten-containing salt, or other methods.

In another embodiment the catalyst support is niobia phosphate. Niobia phosphate may be produced via precipitation from niobium- and phosphate-containing salts through sol-gel processing, impregnation of an aqueous solution of a phosphate solution onto niobium oxide, or other methods.

In another embodiment the catalyst support is titania. The titania may be produced via precipitation from titanium salts, through sol-gel processing, or any other method. The titania may be present in a crystalline form and may include both anatase and rutile crystalline phases. A modifying agent may be added to improve the textural or catalytic properties of the titania. Such modifying agents include, without limitation, sulfate, silica, tungstenate, and oxides of Group IIIB metals (e.g., Ce, La, or Y).

In another embodiment the catalyst support is a transitional alumina, such as theta alumina. The theta alumina may be produced via precipitation from aluminum salts, through sol-gel processing, or any other method. The support may be manufactured through peptization of a suitable aluminum hydroxide, such as bohemite or pseudo-bohemite, with nitric acid in the presence of an organic binder, such as hydroxy-ethyl cellulose. After forming, the support is then calcined at a final temperature between about 900° C. to about 1200° C., or greater than about 1000° C. A modifying agent may be added to improve the textural or catalytic properties of the alumina. Such modifying agents include, without limitation, sulfate, silica, Fe, Ce, La, Cu, Co, Mo, or W.

The support may also be treated or modified to enhance its properties. For example, the support may be treated, as by surface-modification, to modify surface moieties, such as hydrogen and hydroxyl. Surface hydrogen and hydroxyl groups can cause local pH variations that affect catalytic efficiency. The support may also be modified, for example, by treating it with sulfates, phosphates, tungsten, silanes, lanthanides, alkali compounds or alkali earth compounds.

Conventional methods for preparing catalyst systems are well known in the art. Common methods include incipient wetting, evaporative impregnation, chemical vapor deposition, wash-coating, magnetron sputtering techniques, and the like. The method chosen to fabricate the deoxygenation catalyst is not critical to the process, with the proviso that different catalysts and methods of preparation will yield different results, depending upon considerations such as overall surface area, porosity, etc.

To produce the oxygenated compounds, the oxygenated hydrocarbon is combined with water to provide an aqueous feedstock solution having a concentration effective for causing the formation of the desired reaction products. The water-to-carbon ratio on a molar basis may be from about 0.5:1 to about 100:1, including ratios such as 1:1, 2:1, 3:1, 4:1, 5:1, 6:1, 7:1, 8:1, 9:1, 10:1, 15:1, 25:1, 50:1 75:1, 100:1, and any ratios there-between. The feedstock solution may also be characterized as a solution having at least about 1.0 weight percent (wt %) of the total solution as an oxygenated hydrocarbon. For instance, the solution may include one or more oxygenated hydrocarbons, with the total concentration of the oxygenated hydrocarbons in the solution being at least about 1%, 5%, 10%, 20%, 30%, 40%, 50%, 60%, 70%, 80% or greater by weight, including any percentages between, and depending on the oxygenated hydrocarbons used. In one embodiment, the feedstock solution includes at least about 10%, 20%, 30%, 40%, 50%, or 60% of a sugar, such as glucose, fructose, sucrose or xylose, or a sugar alcohol, such as sorbitol, mannitol, glycerol or xylitol, by weight. Water-to-carbon ratios and percentages outside of the above stated ranges are also included.

In one embodiment the feedstock solution is reacted with hydrogen in the presence of the deoxygenation catalyst at temperatures, pressures, and weight hourly space velocities effective to produce the desired oxygenated compounds. The specific oxygenates produced will depend on various factors, including the feedstock solution, reaction temperature, reaction pressure, water concentration, hydrogen concentration, the reactivity of the catalyst, and the flow rate of the feedstock solution as it affects the space velocity (the mass/volume of reactant per unit of catalyst per unit of time), gas hourly space velocity (GHSV), and weight hourly space velocity (WHSV). For example, an increase in flow rate, and thereby a reduction of feedstock exposure to the deoxygenation catalyst over time, will limit the extent of the reactions that may occur, thereby causing increased yield for higher level di- and tri-oxygenates, with a reduction in ketone, alcohol, and cyclic ether yields.

The reaction temperature and pressures may be selected to maintain at least a portion of the feedstock in the liquid phase at the reactor inlet. It is recognized, however, that temperature and pressure conditions may also be selected to more favorably produce the desired products in the vapor-phase. In general, the reaction should be conducted at process conditions wherein the thermodynamics of the proposed reaction are favorable. For instance, the minimum pressure required to maintain a portion of the feedstock in the liquid phase will likely vary with the reaction temperature. As temperatures increase, higher pressures will generally be required to maintain the feedstock in the liquid phase, if desired. Pressures above that required to maintain the feedstock in the liquid phase (i.e., vapor-phase) are also suitable operating conditions.

In general, the reaction may include a temperature gradient to allow partial deoxygenation of the oxygenated hydrocarbon feedstock at temperatures below the caramelization point of the feedstock. Including a temperature gradient helps prevent the oxygenated hydrocarbons in the feedstock from condensing (e.g., caramelizing) on the catalyst and creating a substantial pressure drop across the reactor that can lead to its inoperability. The caramelization point, and therefore the required temperature gradient, will vary depending on the feedstock. In one embodiment, the temperature gradient is from about 80° C. to 300° C., or between about 170° C. to 300° C., or between about 200° C. to 290° C. In another embodiment, a temperature gradient is not employed.

Operating pressures up to about 2500 psig can be used to help maintain the carbon backbone and minimize the amount of light organic acids and ketones that are formed by increasing the product selectivity towards alcohols. By increasing operating pressures, the thermodynamics of the reaction favor alcohols to ketones and organic acids, thereby shifting the product selectivity, maintaining the carbon backbone, and improving product yields. Light organic acids are particularly undesirable products as they are highly corrosive. Producing fewer light organic acids provides more flexibility with regards to materials of construction of a reactor system because corrosion is less of an issue.

In condensed phase liquid reactions, the pressure within the reactor must be sufficient to maintain the reactants in the condensed liquid phase at the reactor inlet. For liquid phase reactions, the reaction temperature may be greater than 100° C., or 110° C., or 120° C., or 130° C., or 140° C. or 150° C., or 160° C., or 170° C., or 180° C., or 190° C., or 200° C., and less than 300° C., or 290° C., or 280° C., or 270° C., or 260° C., or 250° C., or 240° C., or 230° C., or 220° C. The reaction pressure may be greater than about 70 psig, or 85 psig, or 100 psig, or 115 psig, or 130 psig, or 145 psig, or 160 psig, or 175 psig, or 190 psig, or 205 psig, or 220 psig, or 235 psig, or 250 psig, or 265 psig, or 280 psig, or 295 psig, or 310 psig, or 325 psig, or 375 psig, or 425 psig, or 475 psig, or 550 psig, or 625 psig, or 775 psig, or 925 psig, or 1050 psig, and less than 2500 psig, or 2450 psig, or 2400 psig, or 2350 psig, or 2300 psig, or 2250 psig, or 2200 psig, or 2150 psig, or 2100 psig, or 2050 psig, or 2000 psig, or 1950 psig, or 1900 psig, or 1850 psig, or 1800 psig. In certain embodiments, the reaction temperature is between about 120° C. and 300° C., or between about 200° C. and 300° C., or between about 270° C. and 290° C., and the reaction pressure is between about 145 and 2500 psig, or between about 1000 and 2000 psig, or between about 1050 and 1800 psig.

For vapor phase reactions, the reaction may be carried out at a temperature where the vapor pressure of the oxygenated hydrocarbon is at least about 0.1 atm., but in some cases higher (e.g., 350 psi), and the thermodynamics of the reaction are favorable. This temperature will vary depending upon the specific oxygenated hydrocarbon compound used, but is generally greater than about 100° C., or 120° C., or 160° C., or 200° C., or 250° C., and less than about 600° C., or 500° C., or 400° C. for vapor phase reactions. In certain embodiments, the reaction temperature is between about 120° C. and about 500° C., or between about 250° C. and about 400° C.

In general, the reaction should be conducted under conditions where the residence time of the feedstock solution over the catalyst is appropriate to generate the desired products. For example, the WHSV for the reaction may be at least about 0.01 gram of oxygenated hydrocarbon per gram of catalyst per hour, and, in certain cases, the WHSV is about 0.01 to 40.0 g/g hr, including a WHSV of 0.01, 0.025, 0.05, 0.075, 0.1, 0.25, 0.5, 0.75, 1.0, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 6, 7, 8, 9, 10, 11, 12, 13, 14, 15, 20, 25, 30, 35, 40 g/g hr, and ratios between (including 0.77, 0.78, 0.79, 2.61, 2.62, 2.63, etc.).

The hydrogen used in the reaction is may be external hydrogen, but may include in-situ generated hydrogen. The amount (moles) of external hydrogen or recycled hydrogen introduced to the feedstock may be between about 0-2400%, 5-2400%, 10-2400%, 15-2400%, 20-2400%, 25-2400%, 30-2400%, 35-2400%, 40-2400%, 45-2400%, 50-2400%, 55-2400%, 60-2400%, 65-2400%, 70-2400%, 75-2400%, 80-2400%, 85-2400%, 90-2400%, 95-2400%, 98-2400%, 100-2400%, 200-2400%, 300-2400%, 400-2400%, 500-2400%, 600-2400%, 700-2400%, 800-2400%, 900-2400%, 1000-2400%, 1100-2400%, or 1150-2400%, or 1200-2400%, or 1300-2400%, or 1400-2400%, or 1500-2400%, or 1600-2400%, or 1700-2400%, or 1800-2400%, or 1900-2400%, or 2000-2400%, or 2100-2400%, or 2200-2400%, or 2300-2400% of the total number of moles of the oxygenated hydrocarbon(s) in the feedstock, including all intervals between. When the feedstock solution, or any portion thereof, is reacted with in-situ generated hydrogen and external hydrogen or recycled hydrogen, the molar ratio of in-situ generated hydrogen to external hydrogen (or recycled hydrogen) is at least 1:100, 1:50, 1:20; 1:15, 1:10, 1:5; 1:3, 1:2, 1:1, 2:1, 3:1, 5:1, 10:1, 15:1, 20:1, 50:1, 100:1 and ratios between (including 4:1, 6:1, 7:1, 8:1, 9:1, 11:1, 12:1, 13:1, 14:1, 15:1, 16:1, 17:1, 18:1 and 19:1, and vice-versa).

Deoxygenation Product Recycle

Recycle streams may be used to maximize product yields and reduce catalyst deactivation. The product of the deoxygenation reaction includes partially deoxygenated hydrocarbons in addition to the $C_{2+}O_{1+}$ oxygenated compounds. Partially deoxygenated hydrocarbons include $C_{2+}O_{2+}$ hydrocarbons (e.g., disaccharides, monosaccharides, sugars, sugar alcohols, alditols, heavy organic acids, and heavy diols, triols, and other polyols). Recycling these partially deoxygenated hydrocarbons back into the deoxygenation reactor system reduces the carbohydrate concentration entering the deoxygenation reactor system by diluting the carbohydrate-rich feedstock solution with partially deoxygenated hydrocarbons. Diluting the highly reactive carbohydrate feed stream minimizes condensation reactions in the deoxygenation reactor system in which the feedstock condenses on the deoxygenation catalyst, fouling the catalyst, and requiring frequent catalyst changes and/or regeneration. In certain embodiments the recycle to fresh feed weight ratio is in the range of about 0.25-to-1 to 10-to-1, including any ratios between, such as 0.50, 1.00, 2.50, 4.00, 5.00, and 7.50-to-1.

Reactor System

The reactions described herein may be carried out in any reactor of suitable design, including continuous-flow, batch, semi-batch or multi-system reactors, without limitation as to design, size, geometry, flow rates, etc. The reactor system may also use a fluidized catalytic bed system, a swing bed system, fixed bed system, a moving bed system, or a combination of the above. In one embodiment, the process is carried out using a continuous-flow system at steady-state equilibrium.

FIGS. 1A (without an aqueous recycle stream) and 1B (with an aqueous recycle stream) are schematic illustrations showing embodiments for converting a biomass-derived oxygenated hydrocarbon feedstock solution to a final desired product using a single reactor containing a deoxygenation catalyst on a support. In certain embodiments the feedstock solution includes a solvent (e.g., water, recycled partially deoxygenated hydrocarbons, etc.) combined with oxygenated hydrocarbons, such as carbohydrates (e.g., monosaccharides, disaccharides, oligosaccharides, polysaccharides, and starches), sugars (e.g., glucose, sucrose, xylose, etc.), and sugar degradation products (e.g., hydroxymethylfurfural (HMF), levulinic acid, formic acid, and furfural). As described above, in certain embodiments the feedstock may also include ash components, sugar alcohols (e.g., diols, triols, and polyols), extractives, phenolics, etc. In one embodiment the feedstock is fed via a pump to the deoxygenation reactor system having the deoxygenation catalyst on a support, where it subsequently reacts with hydrogen to generate oxygenated compounds (e.g., monooxygenates, dioxygenates, ketones, carboxylic acids, cyclic ethers, aldehydes, and alcohols).

In certain embodiments the effluent stream from the reactor contains a mixture of water, hydrogen, carbon dioxide, light hydrocarbons (e.g., alkanes have four or fewer carbon atoms, such as methane, ethane, propane, and butane), monooxygenates, dioxygenates, alcohols, ketones, carboxylic acids, aldehydes, cyclic ethers, and unreacted feedstock. In one embodiment the mixture is passed through a three-phase separator to separate the non-condensed gases (such as hydrogen, carbon dioxide, methane, ethane, and propane) from the deoxygenation organic products stream and the deoxygenation aqueous stream. The non-condensed gases are removed via a deoxygenation off-gas stream. The non-condensable stream can be either combusted to create process heat (i.e., heat for driving the reaction in the deoxygenation reactor), or sent to a separation system where hydrogen can be recovered for recycle back to the hydrogen stream. The deoxygenation aqueous stream, containing partially deoxygenated hydrocarbons, may be recycled back to the reactor inlet. A deoxygenation aqueous stream, including some monooxygenates (e.g., alcohols), can be used to prevent a build-up of water in the reactor system.

Condensation

The oxygenated compounds can be collected and used in industrial applications, or converted into $C_{4+}$ compounds by condensation reactions catalyzed by a condensation catalyst. Without being limited to any specific theories, it is believed that the condensation reactions generally consist of a series of steps involving: (a) the dehydration of oxygenates to alkenes; (b) oligomerization of the alkenes; (c) cracking reactions; (d) cyclization of larger alkenes to form aromatics; (e) alkane isomerization; (f) hydrogen-transfer reactions to form alkanes. The reactions may also consist of a series of steps involving: (1) aldol condensation to form a β-hydroxyketone or β-hydroxyaldehyde; (2) dehydration of the β-hydroxyketone or β-hydroxyaldehyde to form a conjugated enone; (3) hydrogenation of the conjugated enone to form a ketone or aldehyde, which may participate in further condensation reactions or conversion to an alcohol or hydrocarbon; and (4) hydrogenation of carbonyls to alcohols, or vice-versa. Other condensation reactions may occur in parallel, including aldol condensation, prins reactions, ketonization of acids, and Diels-Alder condensation.

The condensation catalyst will generally be a catalyst capable of forming longer chain compounds by linking two oxygen containing species, or other functionalized compounds (e.g., olefins), through a new carbon-carbon bond, and converting the resulting compound to a hydrocarbon, alcohol or ketone. The condensation catalyst may include, without limitation, carbides, nitrides, zirconia, alumina, silica, aluminosilicates, phosphates, zeolites, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may include the above alone or in combination with a modifier, such as Ce, La, Y, Sc, P, B, Bi, Li, Na, K, Rb, Cs, Mg, Ca, Sr, Ba, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

In certain embodiments the condensation catalyst may include, without limitation, carbides, nitrides, zirconia, alumina, silica, aluminosilicates, phosphates, zeolites (e.g., ZSM-5, ZSM-11, ZSM-12, ZSM-22, ZSM-23, ZSM-35 and ZSM-48), titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and combinations thereof. The condensation catalyst may also include a metal, such as Cu, Ag, Au, Pt, Ni, Fe, Co, Ru, Zn, Cd, Ga, In, Rh, Pd, Ir, Re, Mn, Cr, Mo, W, Sn, Os, alloys and combinations thereof, to provide a metal functionality.

The condensation catalyst may be self-supporting (i.e., the catalyst does not need another material to serve as a support), or may require a separate support suitable for suspending the catalyst in the reactant stream. In certain embodiments the support is selected from the group consisting of alumina, silica, and zirconia. In other embodiments, particularly when the condensation catalyst is a powder, the catalyst system may include a binder to assist in forming the catalyst into a desirable catalyst shape. Applicable forming processes include extrusion, pelletization, oil dropping, or other known processes. Zinc oxide, alumina, and a peptizing agent may also be mixed together and extruded to produce a formed material. After drying, this material is calcined at a temperature appropriate for formation of the catalytically active phase, which usually requires temperatures in excess of 350° C. Other catalyst supports may include those described in further detail below.

In one embodiment the condensation reaction may be performed using a catalyst having acidic functionality. The acid catalysts may include, without limitation, aluminosilicates (zeolites), silica-alumina phosphates (SAPO), aluminum phosphates (ALPO), amorphous silica alumina, zirconia, sulfated zirconia, tungstated zirconia, tungsten carbide, molybdenum carbide, titania, acidic alumina, phosphated alumina, phosphated silica, sulfated carbons, phosphated carbons, acidic resins, heteropolyacids, inorganic acids, and combinations thereof. In one embodiment, the catalyst may also include a modifier, such as Ce, La, Y, Li, Na, K, Rb, Cs, Mg, Ca, Sr, Ba, P, B, Bi, and combinations thereof. The catalyst may also be modified by the addition of a metal, such as Cu, Ag, Au, Pt, Ni, Fe, Co, Ru, Rh, Zn, Ga, In, Pd, Ir, Re, Mn, Cr, Mo, W, Sn, Os, alloys and combinations thereof, to provide metal functionality, and/or sulfides and oxides of Ti, Zr, V, Nb, Ta, Mo, Cr, W, Mn, Re, Al, Ga, In, Fe, Co, Ir, Ni, Si, Cu, Zn, Sn, P, and combinations thereof. Tungstated zirconia, an exemplary catalyst for use in the present process, may be modified with Cu, Pd, Ag, Pt, Ru, Ni, Sn and combinations thereof. The acid catalyst may be homogenous, self-supporting or adhered to any one of the supports further described below, including supports containing carbon, silica, alumina, zirconia, titania, vanadia, ceria, heteropolyacids, alloys and mixtures thereof.

The condensation catalyst may be a zeolite catalyst. The term "zeolite" as used herein refers not only to microporous crystalline aluminosilicate, but also microporous crystalline metal-containing aluminosilicate structures, such as galloaluminosilicates and gallosilicates. In such instances, In, Zn, Fe, Mo, Ag, Au, Ni, P, Y, Ta, and lanthanides may be exchanged onto zeolites to provide the desired activity. Metal functionality may be provided by metals such as Cu, Ag, Au, Pt, Ni, Fe, Co, Ru, Zn, In, Rh, Pd, Ir, Re, Mn, Cr, Mo, W, Sn, Os, alloys and combinations thereof.

The condensation catalyst may include one or more zeolite structures comprising cage-like structures of silica-alumina. Zeolites are crystalline microporous materials with well-defined pore structures. Zeolites contain active sites, usually acid sites, which can be generated in the zeolite framework. The strength and concentration of the active sites can be tailored for particular applications. Examples of suitable zeolites for condensing secondary alcohols and alkanes may comprise aluminosilicates, optionally modified with cations, such as Ga, In, Zn, Mo, and mixtures of such cations, as described, for example, in U.S. Pat. No. 3,702,886, which is incorporated herein by reference. As recognized in the art, the structure of the particular zeolite or zeolites may be altered to provide different amounts of various hydrocarbon species in the product mixture. Depending on the structure of the zeolite catalyst, the product mixture may contain various amounts of aromatic and cyclic hydrocarbons.

Examples of suitable zeolite catalysts include ZSM-5, ZSM-11, ZSM-12, ZSM-22, ZSM-23, ZSM-35 and ZSM-48. Zeolite ZSM-5, and the conventional preparation thereof, is described in U.S. Pat. Nos. 3,702,886; Re. 29,948 (highly siliceous ZSM-5); U.S. Pat. No. 4,100,262 and U.S. Pat. No. 4,139,600, all incorporated herein by reference. Zeolite ZSM-11, and the conventional preparation thereof, is described in U.S. Pat. No. 3,709,979, which is also incorporated herein by reference. Zeolite ZSM-12, and the conventional preparation thereof, is described in U.S. Pat. No. 3,832,449, incorporated herein by reference. Zeolite ZSM-23, and the conventional preparation thereof, is described in U.S. Pat.

No. 4,076,842, incorporated herein by reference. Zeolite ZSM-35, and the conventional preparation thereof, is described in U.S. Pat. No. 4,016,245, incorporated herein by reference. Another preparation of ZSM-35 is described in U.S. Pat. No. 4,107,195, the disclosure of which is incorporated herein by reference. ZSM-48, and the conventional preparation thereof, is taught by U.S. Pat. No. 4,375,573, incorporated herein by reference. Other examples of zeolite catalysts are described in U.S. Pat. No. 5,019,663 and U.S. Pat. No. 7,022,888, also incorporated herein by reference. An exemplary condensation catalyst is a ZSM-5 zeolite modified with Cu, Pd, Ag, Pt, Ru, Ni, Sn, or combinations thereof.

As described in U.S. Pat. No. 7,022,888, the condensation catalyst may be a bifunctional pentasil zeolite catalyst including at least one metallic element from the group of Cu, Ag, Au, Pt, Ni, Fe, Co, Ru, Zn, Cd, In, Rh, Pd, Ir, Re, Mn, Cr, Mo, W, Sn, Os, alloys and combinations thereof, or a modifier from the group of In, Zn, Fe, Mo, Au, Ag, Y, Sc, Ni, P, Ta, lanthanides, and combinations thereof. The zeolite may have strong acidic sites, and may be used with reactant streams containing an oxygenated hydrocarbon at a temperature of below 580° C. The bifunctional pentasil zeolite may have ZSM-5, ZSM-8 or ZSM-11 type crystal structure consisting of a large number of 5-membered oxygen-rings (i.e., pentasil rings). In one embodiment the zeolite will have a ZSM-5 type structure.

Alternatively, solid acid catalysts such as alumina modified with phosphates, chloride, silica, and other acidic oxides may be used in the process. Also, sulfated zirconia, phosphated zirconia, titania zirconia, or tungstated zirconia may provide the necessary acidity. Re and Pt/Re catalysts are also useful for promoting condensation of oxygenates to $C_{5+}$ hydrocarbons and/or $C_{5+}$ mono-oxygenates. The Re is sufficiently acidic to promote acid-catalyzed condensation. In certain embodiments, acidity may also be added to activated carbon by the addition of either sulfates or phosphates.

The specific $C_{4+}$ compounds produced will depend on various factors, including, without limitation, the type of oxygenated compounds in the reactant stream, condensation temperature, condensation pressure, the reactivity of the catalyst, and the flow rate of the reactant stream as it affects the space velocity, GHSV, LHSV, and WHSV. In certain embodiments, the reactant stream is contacted with the condensation catalyst at a WHSV that is appropriate to produce the desired hydrocarbon products. In one embodiment the WHSV is at least about 0.1 grams of volatile ($C_{2+}O_{1-2}$) oxygenates in the reactant stream per gram catalyst per hour. In another embodiment the WHSV is between about 0.1 to 10.0 g/g hr, including a WHSV of 1, 2, 3, 4, 5, 6, 7, 8, 9, 10 g/g hr, and increments between.

In certain embodiments the condensation reaction is carried out at a temperature and pressure at which the thermodynamics of the proposed reaction are favorable. For volatile $C_{2+}O_{1-2}$ oxygenates the reaction may be carried out at a temperature where the vapor pressure of the volatile oxygenates is at least about 0.1 atm. (and, in certain cases, a good deal higher). The condensation temperature will vary depending upon the specific composition of the oxygenated compounds. The condensation temperature will generally be greater than 80° C., or 100° C., or 125° C., or 150° C., or 175° C., or 200° C., or 225° C., or 250° C., and less than 600° C., or 500° C., or 450° C., or 425° C., or 375° C., or 325° C., or 275° C. For example, the condensation temperature may be between about 80° C. to 500° C., or between about 125° C. to 450° C., or between about 250° C. to 425° C. The condensation pressure will generally be greater than 0 psig, or 10 psig, or 100 psig, or 200 psig, and less than 1500 psig, or 1400 psig, or 1300 psig, or 1200 psig, or 1100 psig, or 1000 psig, or 900 psig, or 700 psig. For example, the condensation pressure may be greater than about 0.1 atm., or between about 0 and 1500 psig, or between about 0 and 1200 psig.

Condensation Products

The deoxygenation and condensation reactions can be used in the production of $C_{4+}$ alkanes, $C_{4+}$ alkenes, $C_{5+}$ cycloalkanes, $C_{5+}$ cycloalkenes, aryls, fused aryls, polycyclic molecules, $C_{4+}$ alcohols, $C_{4+}$ ketones, $C_{4+}$ furans and mixtures thereof. The $C_{4+}$ alkanes and $C_{4+}$ alkenes have from 4 to 30 carbon atoms ($C_{4-30}$ alkanes and $C_{4-30}$ alkenes) and may be branched or straight chained alkanes or alkenes. The $C_{4+}$ alkanes and $C_{4+}$ alkenes may also include fractions of $C_{4-9}$, $C_{7-14}$, $C_{12-24}$ alkanes and alkenes, respectively, with the $C_{4-9}$ fraction directed to gasoline, the $C_{7-16}$ fraction directed to jet fuels, and the $C_{11-24}$ fraction directed to diesel fuel and other industrial applications. Examples of various $C_{4+}$ alkanes and $C_{4+}$ alkenes include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4-trimethylpentane, 2,3-dimethyl hexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The $C_{5+}$ cycloalkanes and $C_{5+}$ cycloalkenes have from 5 to 30 carbon atoms and may be unsubstituted, mono-substituted or multi-substituted. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-12}$ alkyl, a straight chain $C_{1-12}$ alkyl, a branched $C_{3-12}$ alkylene, a straight chain $C_{1-12}$ alkylene, a straight chain $C_{2-12}$ alkylene, a phenyl or a combination thereof. By way of further example, at least one of the substituted groups include a branched $C_{3-4}$ alkyl, a straight chain $C_{1-4}$ alkyl, a branched $C_{3-4}$ alkylene, straight chain $C_{1-4}$ alkylene, straight chain $C_{2-4}$ alkylene, a phenyl or a combination thereof. Examples of desirable $C_{5+}$ cycloalkanes and $C_{5+}$ cycloalkenes include, without limitation, cyclopentane, cyclopentene, cyclohexane, cyclohexene, methyl-cyclopentane, methyl-cyclopentene, ethyl-cyclopentane, ethyl-cyclopentene, ethyl-cyclohexane, ethyl-cyclohexene, propyl-cyclohexane, butyl-cyclopentane, butyl-cyclohexane, pentyl-cyclopentane, pentyl-cyclohexane, hexyl-cyclopentane, hexyl-cyclohexane, and isomers thereof.

Aryls will generally consist of an aromatic hydrocarbon in either an unsubstituted (phenyl), mono-substituted or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-12}$ alkyl, a straight chain $C_{1-12}$ alkyl, a branched $C_{3-12}$ alkylene, a straight chain $C_{2-12}$ alkylene, a phenyl or a combination thereof. By way of further example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various aryls include, without limitation, benzene, toluene, xylene (dimethylbenzene), ethyl benzene, para xylene, meta xylene, ortho xylene, $C_{9+}$ aromatics, butyl benzene, pentyl benzene, hexyl benzene, heptyl benzene, oxtyl benzene, nonyl benzene, decyl benzene, undecyl benzene, and isomers thereof.

Fused aryls will generally consist of bicyclic and polycyclic aromatic hydrocarbons, in either an unsubstituted, mono-substituted, or multi-substituted form. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, naphthalene, anthracene, and isomers thereof.

Polycyclic compounds will generally consist of bicyclic and polycyclic hydrocarbons, in either an unsubstituted, mono-substituted, or multi-substituted form. Although polycyclic compounds include fused aryls, as used herein the polycyclic compounds generally have at least one saturated or partially saturated ring unless clear from context that the term includes fused aryls. In the case of mono-substituted and multi-substituted compounds, the substituted group may include a branched $C_{3+}$ alkyl, a straight chain $C_{1+}$ alkyl, a branched $C_{3+}$ alkylene, a straight chain $C_{2+}$ alkylene, a phenyl or a combination thereof. By way of example, at least one of the substituted groups include a branched $C_{3-4}$ alkyl, a straight chain $C_{1-4}$ alkyl, a branched $C_{3-4}$ alkylene, straight chain $C_{2-4}$ alkylene, a phenyl or a combination thereof. Examples of various fused aryls include, without limitation, tetrahydronaphthalene and decahydronaphthalene, and isomers thereof.

The $C_{4+}$ alcohols may also be cyclic, branched or straight chained, and have from 4 to 30 carbon atoms. In general, the $C_{4+}$ alcohols may be a compound according to the formula $R^1$—OH, wherein $R^1$ is a member selected from the group consisting of a branched $C_{4+}$ alkyl, straight chain $C_{4+}$ alkyl, a branched $C_{4+}$ alkylene, a straight chain $C_{4+}$ alkylene, a substituted $C_{5+}$ cycloalkane, an unsubstituted $C_{5+}$ cycloalkane, a substituted $C_{5+}$ cycloalkene, an unsubstituted $C_{5+}$ cycloalkene, an aryl, a phenyl and combinations thereof. Examples of desirable $C_{4+}$ alcohols include, without limitation, butanol, pentanol, hexanol, heptanol, octanol, nonanol, decanol, undecanol, dodecanol, tridecanol, tetradecanol, pentadecanol, hexadecanol, heptyldecanol, octyldecanol, nonyldecanol, eicosanol, uneicosanol, doeicosanol, trieicosanol, tetraeicosanol, and isomers thereof.

The $C_{4+}$ ketones may also be cyclic, branched or straight chained, and have from 4 to 30 carbon atoms. In general, the $C_{4+}$ ketone may be a compound according to the formula

wherein $R^3$ and $R^4$ are independently a member selected from the group consisting of a branched $C_{3+}$ alkyl, a straight chain $C_{1+}$ alkyl, a branched $C_{3+}$ alkylene, a straight chain $C_{2+}$ alkylene, a substituted $C_{5+}$ cycloalkane, an unsubstituted cycloalkane, a substituted $C_{5+}$ cycloalkene, an unsubstituted $C_{5+}$ cycloalkene, an aryl, a phenyl and a combination thereof. Examples of desirable $C_{4+}$ ketones include, without limitation, butanone, pentanone, hexanone, heptanone, octanone, nonanone, decanone, undecanone, dodecanone, tridecanone, tetradecanone, pentadecanone, hexadecanone, heptyldecanone, octyldecanone, nonyldecanone, eicosanone, uneicosanone, doeicosanone, trieicosanone, tetraeicosanone, and isomers thereof.

In certain embodiments, the lighter fractions of the above, primarily $C_4$-$C_{12}$, may be separated for gasoline use. Moderate fractions, such as $C_7$-$C_{16}$, may be separated for jet fuel, while heavier fractions, i.e., $C_{11}$-$C_{24}$, may be separated for diesel use. The heaviest fractions may be used as lubricants or cracked to produce additional gasoline and/or diesel fractions. The $C_{4+}$ compounds may also find use as industrial chemicals, whether as an intermediate or an end product. For example, the aryls toluene, xylene, ethyl benzene, para xylene, meta xylene, ortho xylene may find use a chemical intermediates for the product of plastics and other products. Meanwhile, the $C_{9+}$ aromatics and fused aryls, such as naphthalene, anthracene, tetrahydronaphthalene, and decahydronaphthalene, may find use as solvents in industrial processes.

Liquid Fuels and Chemicals

The $C_{4+}$ compounds derived from the deoxygenation and condensation reactions as described above can be fractionated and used in liquid fuels, such as gasoline, jet fuel (kerosene) or diesel fuel. The $C_{4+}$ compounds can also be fractionated and used in chemical processes, such as those common to the petro-chemical industry. For example, the product stream from the process can be fractionated to collect xylenes for use in the production of phthalic acid, polyethylene terephthalate (PET), and ultimately renewable plastics or solvents. Benzene can also be collected and processed for the production of renewable polystyrenes, polycarbonates, polyurethane, epoxy resins, phenolic resins, and nylon. Toluene can be collected and processed for the production of toluene diisocyanate, and ultimately renewable solvents, polyurethane foam or TNT, among others.

In one embodiment, the $C_{4+}$ compounds derived from the process are separated into various distillation fractions by any means known for liquid fuel compositions. In such applications, the product stream having at least one $C_{4+}$ compound derived from the process is separated into more than one distillation fraction, wherein at least one of the distillation fractions is a lighter, moderate or heavier fraction. The lighter fractions, primarily $C_4$-$C_9$ i.e., $C_4$, $C_5$, $C_6$, $C_7$, $C_8$, and $C_9$, may be separated for gasoline use. The moderate fractions, primarily $C_7$-$C_{14}$, i.e., $C_7$, $C_8$, $C_9$, $C_{10}$, $C_{11}$, $C_{12}$, $C_{13}$, and $C_{14}$, may be separated for use as kerosene, e.g., for jet fuel use. Heavier fractions, primarily $C_{12}$-$C_{24}$, i.e., $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, and $C_{24}$, may be separated for diesel fuel use. The heaviest fractions, $C_{25+}$ and $C_{30+}$, i.e., $C_{25}$, $C_{26}$, $C_{27}$, $C_{28}$, $C_{29}$, $C_{30}$, $C_{31}$, $C_{32}$, $C_{33}$, $C_{34}$, $C_{35}$, etc., may be used as lubricants, fuel oils, or may be cracked to produce additional fractions for use in gasoline, kerosene and/or diesel fractions.

Because the $C_{4+}$ compounds are derived from biomass, the age of the compounds, or fractions containing the compounds, is less than 500 years old, less than 100 years old, less than 40 years old, and less than 20 years old, as calculated from the carbon 14 concentration of the component.

The following examples are to be illustrative and should not be construed to limit the scope of protection sought, which is defined by the appended claims.

EXAMPLES

Example A

Table 1 provides ash component analyses for five feedstock sugar compositions.

TABLE 1

Ash component analyses for five feedstocks

|  | Exemplary hydrolysate | Commercial fermentation grade glucose corn syrup | Commercial 42 DE refined corn syrup | #11 raw cane sugar | Commercial #5 sugar |
|---|---|---|---|---|---|
|  | RESULT (PPM of total solids) | | | | |
| Al | 32 | <0.5 | <0.5 | <0.5 | 4 |
| B | <0.5 | <0.5 | <0.5 | 24 | <0.5 |
| Ba | nt | <0.5 | <0.5 | 50 | <0.5 |
| Ca | 3474 | 48 |  | 2565 | 3 |
| Cu | <0.5 | <0.5 | <0.5 | 7 | 4 |
| Fe | 3 | <0.5 | <0.5 | 21 | 0 |
| K | 921 | 93 | <0.5 | 7296 | 26 |
| Mg | 733 | 57 | <0.5 | 994 | 4 |
| Mn | 2 | <0.5 | 0 | 10 | 4 |
| Na | 220 | 245 | 2 | 381 | 7 |
| P | 50 | 154 | 17 | 379 | 0 |
| S | 35 | 246 | 2 | 794 | 16 |
| Si | 52 | 6 | 4 | 144 | 0 |
| Zn | 9 | <0.5 | <0.5 | 30 | <0.5 |

Example B

Table 2 provides ash component analysis for five samples having reduced ash levels. The results in Table 2 indicate the attainment of low sulfur and phosphorus levels. This suggests that these exemplary samples will exhibit a low tendency to foul or poison catalyst employed in the conversion processes.

TABLE 2

Ash component analyses for exemplary feedstocks

|  | Sample 1 | Sample 2 | Sample 3 | Sample 4 | Sample 5 | Sample 6 | Sample 8 |
|---|---|---|---|---|---|---|---|
|  | RESULT (PPM of total solids) | | | | | | |
| Al | nt | nt | nt | nt | <0.5 | <0.5 | <0.5 |
| B | <0.5 | <0.5 | <0.5 | <0.5 | <0.5 | <0.5 | <0.5 |
| Ba | <0.5 | <0.5 | <0.5 | <0.5 | <0.5 | <0.5 | nt |
| Ca | 2 | <0.5 | 1 | <0.5 | 9 | 9 | 2 |
| Cu | <0.5 | <0.5 | <0.5 | <0.5 | <0.5 | <0.5 |  |
| Fe | <0.5 | <0.5 | <0.5 | <0.5 | 2 | 3 | <0.5 |
| K | <0.5 | <0.5 | <0.5 | <0.5 | <0.5 | <0.5 | <0.5 |
| Mg | <0.5 | <0.5 | <0.5 | <0.5 | 3 | 4 | 4 |
| Mn | <0.5 | <0.5 | <0.5 | <0.5 | <0.5 | <0.5 | <0.5 |
| Na | 5 | 5 | 5 | 5 | 58 | 69 | 8 |
| P | <0.5 | <0.5 | <0.5 | <0.5 | <0.5 | <0.5 | <0.5 |
| S | <1.5 | <1.5 | <1.5 | <1.5 | 4 | 5 | <1.5 |

Example C

Three deoxygenation catalysts (palladium-molybdenum-tin, palladium-ruthenium, and palladium-silver, all on tungstated zirconia supports) were tested to determine the impact of feedstock concentration on deoxygenation catalyst performance, specifically in the conversion of a glucose solution to monooxygenates (e.g., alcohols and ketones). Before the feedstock was introduced, each of the catalysts were reduced using hydrogen at a space velocity of 700 hr$^{-1}$, a 2 hour temperature gradient to 320° C., followed by a 1 hour hydrogen soak. A shell-in-tube reactor system as described in U.S. Pat. No. 7,767,867 to Cortright, which is incorporated herein by reference, was used under the following conditions: a reactor outlet temperature of 270° C.; a reactor pressure of 1050 psig; and a liquid hour space velocity (LHSV) of 2 mL feed per mL catalyst per hour. The hydrogen was provided at a minimum H$_2$/carbon molar ratio of 2.

Figure 2:
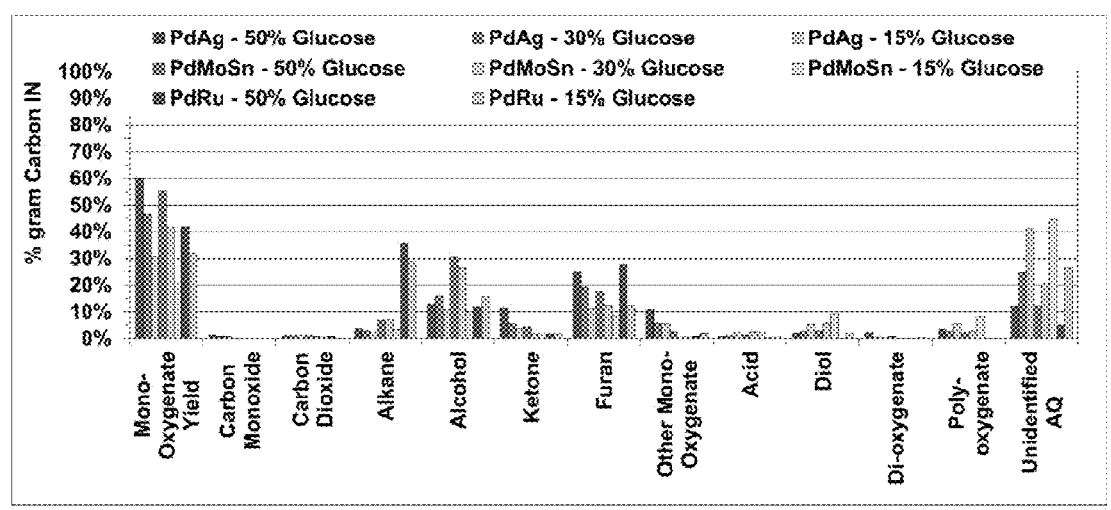
FIG. 2 is an exemplary product distribution illustrating the effect of feedstock concentration on the product profile for three different deoxygenation catalysts.

FIG. 2 illustrates the relationship between monooxygenates yield (defined below) and feedstock concentration for each of the three deoxygenation catalysts. In all cases, glucose conversion was complete, but as concentration decreased, the amount of unidentified aqueous, typically partially deoxygenated sugar species, increases. The increase in partially deoxygenated species is a result of decreased catalyst activity with decreasing sugar concentration.

$$\text{Monooxygenate Yield} = \frac{\text{g Monooxygenate in Product}}{\text{g Feedstock Substrate (ie Glucose)}}$$

Unidentified Aqueous = g Total Carbon in Aqueous − g Speciated Carbon in Aqueous

Example D

A deoxygenation catalyst comprising palladium, molybdenum, tin, and tungsten metals supported on a monoclinic zirconia support was used to test the conversion of three aqueous sugar feedstock solutions to monooxygenates. Before the feedstock was introduced, the catalyst was reduced using hydrogen at a space velocity of 600 hr$^{-1}$, a 2 hour temperature gradient to 300° C., followed by a 1 hour hydrogen soak. A shell-in-tube reactor system as described in U.S. Pat. No. 7,767,867 to Cortright, which is incorporated herein by reference, was used under the following conditions: a reactor outlet temperature of 270-280° C.; a reactor pressure of 1050 psig; and a weight hour space velocity (WHSV) between 0.75 and 1.00 grams of sugar per gram of catalyst per hour. The hydrogen was provided at an H$_2$/Carbon molar ratio of 2.

Table 3 includes a breakdown of common compound classes produced via deoxygenation. In all cases, complete conversion of the sugars in the feedstock was achieved resulting in similar product profiles. Alcohols and cyclic ethers comprise the majority of monooxygenates produced with overall monooxygenates yields varying between 50 and 60%.

TABLE 3

Deoxygenation product breakdown with various sugar feedstocks. Concentrations are represented as a weight percentage of the total carbon entering the system.

| Feed | 45 wt % Glucose 15 wt % Xylose | 50 wt % Glucose | 60 wt % 43 DE Corn Syrup |
|---|---|---|---|
| Temperature (° C.) | 280 | 270 | 270 |
| WHSV (1/hr.) | 0.75 | 1.00 | 0.75 |
| CO + CO$_2$ | 1.8% | 2.2% | 1.6% |
| Alkane | 10.8% | 10.3% | 11.3% |
| Alcohol | 22.3% | 27.0% | 20.6% |
| Ketone | 1.8% | 0.8% | 2.2% |

TABLE 3-continued

Deoxygenation product breakdown with various sugar feedstocks.
Concentrations are represented as a weight percentage
of the total carbon entering the system.

| Feed | 45 wt % Glucose 15 wt % Xylose | 50 wt % Glucose | 60 wt % 43 DE Corn Syrup |
|---|---|---|---|
| Cyclic Ether | 23.9% | 29.9% | 27.2% |
| Acid | 1.6% | 2.2% | 1.8% |
| Diol | 6.3% | 1.2% | 3.2% |
| Polyoxygenate | 1.4% | 0.7% | 2.7% |
| Monooxygenate Yield | 49.6% | 59.4% | 52.0% |

Table 4 provides the carbon chain length for the products from the three sugar feedstocks. The carbon distribution for the corn syrup and glucose feeds are very similar with the majority of the products maintaining the $C_6$ carbon backbone. Similarly, products containing five carbons are more prevalent in the products with the xylose-containing feedstock. The mixed feedstock, when compared to the glucose and corn syrup feedstocks, shows a higher prevalence of retro aldol condensation ($C_2$ and $C_3$) products that are produced from the five carbon sugar.

TABLE 4

Carbon chain length distribution for various sugar feedstocks.
Concentrations are represented as a weight percentage
of the total carbon entering the system.

| Feed | 45 wt % Glucose 15 wt % Xylose | 50 wt % Glucose | 60 wt % 43 DE Corn Syrup |
|---|---|---|---|
| Temperature (° C.) | 280 | 270 | 270 |
| WHSV (1/hr.) | 0.75 | 1.00 | 0.75 |
| CO + $CO_2$ | 1.8% | 2.2% | 1.6% |
| $C_1$ | 0.3% | 0.1% | 0.1% |
| $C_2$ | 4.5% | 3.1% | 2.7% |
| $C_3$ | 14.5% | 9.6% | 9.1% |
| $C_4$ | 5.3% | 4.1% | 4.1% |
| $C_5$ | 12.8% | 7.8% | 9.7% |
| $C_6$ | 31.5% | 46.2% | 45.9% |
| $C_{7+}$ | 4.0% | 6.7% | 1.8% |
| Unidentified Aqueous | 19.7% | 14.0% | 21.2% |

Example E

A 50 wt % sugar feedstock comprising an exemplary composition was processed using a recycle deoxygenation reactor followed by an acid condensation (AC) reactor as illustrated in FIG. 3.

A platinum and rhenium catalyst on a monoclinic zirconia support was used in the deoxygenation reactor, while a nickel-modified ZSM-5 catalyst was used in the AC reactor.

The deoxygenation reactor was operated with an outlet temperature of 260° C. and a pressure of 1050 psig. The AC reactor was operated at a temperature between about 370° C. and 375° C. with an operating pressure of 75 psig. The feedstock was provided at a WHSV of 0.33 grams of feed per grams of deoxygenation catalyst per hour and the recycle to fresh feed ratio for the deoxygenation reactor was 1:1 on a weight basis. A hydrogen co-feed was used at a ratio of 8 mol $H_2$ to 1 mol glucose equivalent fed.

The exemplary sugar compositions were derived from pine biomass using concentrated hydrochloric acid hydrolysis. The composition of a 70 wt % exemplary sugar that was diluted to 50 wt % before being fed into the reactor is shown in Table 5 with the contaminant concentrations in Table 6.

TABLE 5

Exemplary sugar feedstock composition

| Feed Component | % |
|---|---|
| Glucose | 29.2 |
| Mannose | 20.4 |
| Xylose | 10.4 |
| Arabinose | 2.6 |

TABLE 6

Phosphorus and sulfur concentrations of the exemplary composition

| Contaminant | P | S |
|---|---|---|
| Concentration (ppm) | BDL | 3.2 |

Figure 4:
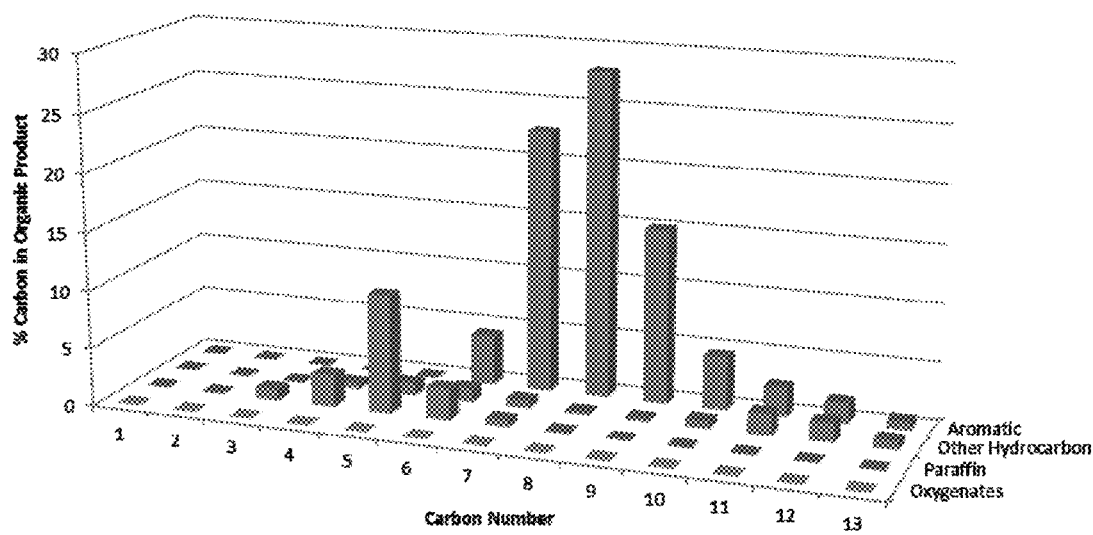
FIG. 4 is a chart illustrating the product distribution, including species and carbon number, for a gasoline range product produced according to one embodiment.

FIG. 4 shows species and carbon number distribution for gasoline range product with carbon numbers typically of four to ten. The product was highly aromatic and is similar to a reformate product from a conventional petroleum refinery.

Example F

A feedstock solution comprising 50 wt % of an exemplary sugar composition was processed using a recycle deoxygenation reactor followed by a dehydration-oligomerization (DHOG) reactor. The deoxygenation catalyst consisted of palladium, molybdenum, and tin metals on a tungstated zirconia support. The DHOG catalyst consisted of palladium and gold metals on a tungstated zirconia support. A nickel oxide on alumina catalyst was used to hydrotreat the product from the DHOG reactor; the hydrotreated product was distilled to isolate only the jet fuel range material.

The deoxygenation reactor was operated at an outlet temperature of 250° C. and a pressure of 1050 psig. The DHOG reactor was operated at an outlet temperature of 290° C. and a pressure of 600 psig. The feedstock was provided at a WHSV of 0.74 grams of feed per grams of deoxygenation catalyst per hour and the recycle to fresh feed ratio for the recycle deoxygenation reactor was 4:1 on a weight basis. A hydrogen co-feed was used at a ratio of 10 mol $H_2$ to 1 mol glucose equivalent fed. The hydrotreating reactor was operated at a temperature of 290° C., a pressure of 800 psig, and a WHSV of 3 grams of feed per grams of catalyst per hour.

The exemplary sugar compositions were derived from pine biomass using concentrated hydrochloric acid hydrolysis. The composition of a 70 wt % exemplary sugar that was diluted to 50 wt % before being fed into the reactor is shown in Table 7 with the contaminant concentrations in Table 8.

TABLE 7

Exemplary sugar feedstock composition

| Feed Component | % |
|---|---|
| Glucose | 31.3 |
| Mannose | 13.3 |
| Xylose | 4.38 |
| Arabinose | 1.18 |

TABLE 8

Phosphorus and sulfur concentrations of the exemplary composition

| Contaminant | P | S |
|---|---|---|
| Concentration (ppm) | BDL | BDL |

Figure 5:
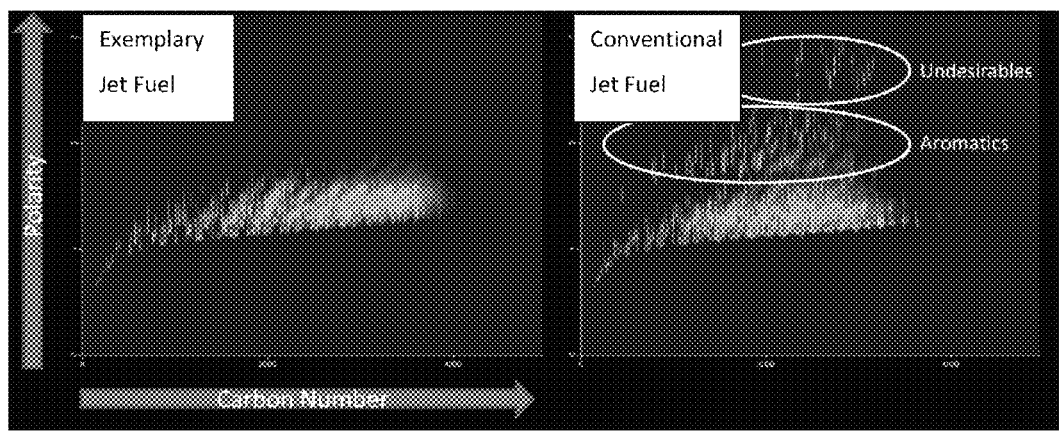
FIG. 5 is a comparison of a conventional jet fuel to a jet fuel produced according to one embodiment.

FIG. 5 compares the final hydrotreated and distilled jet fuel product from the exemplary sugar feedstock to a conventional jet fuel sample. The sample produced with the exemplary sugar feedstock is primarily paraffins and naphthenes, and does not include many aromatics or undesirable components that can lead to deposits and build up in jet engines.

The sample produced with the sugar feedstock was also analyzed by the Air Force Research Lab (AFRL) at Wright Patterson Air Force Base and has satisfactorily completed testing through CAAFI Fuel Readiness Level 3. The product has excellent cold flow properties, high thermal stability, and high energy density. The physical properties meet anticipated synthetic fuel specifications (ASTM D 7566). Detailed testing results are shown in Table 9.

TABLE 9

Detailed testing results of Jet fuel

| Specification Test | MIL-DTL-83133G Spec Requirement (JP-8) | Virent Jet RPN | Typical JP-8 (reference) |
|---|---|---|---|
| Aromatics, vol % | ≤25 | 1.5 | 18.8 |
| Olefins, vol % | | 0.6 | 0.8 |
| Heat of Combustion (measured), MJ/Kg | ≥42.8 | 43.3 | 43.3 |
| Distillation: | | | |
| IBP, ° C. | | 142 | 159 |
| 10% recovered, ° C. | ≤205 | 164 | 182 |
| 20% recovered, ° C. | | 174 | 189 |
| 50% recovered, ° C. | | 203 | 208 |
| 90% recovered, ° C. | | 260 | 244 |
| EP, ° C. | ≤300 | 290 | 265 |
| Residue, % vol | ≤1.5 | 2 | 1.3 |
| Loss, % vol | ≤1.5 | 0 | 0.8 |
| T90 – T10, ° C. | ≥22 | 86 | 62 |
| Flash point, ° C. | ≥38 | 40 | 51 |
| Freeze Point, ° C. | ≤−47 | <−60 | −50 |
| API Gravity @ 60° F. | 37.0-51.0 | 45.4 | 44.4 |
| Density @ 15° C., kg/L | 0.775-0.840 | 0.800 | 0.804 |
| Thermal Stability @ 325° C. or 260° C.** | | | |
| Tube Deposit Rating | <3 | 1 | 1** |
| Change in Pressure, mmHg | ≤25 | 0 | 2 |

**JP-8 thermal stability test is done at 260° C., where as alternative fuels, including the Virdia/Virent fuel, are required to pass the thermal stability test at 325° C.

Example G

An aqueous feedstock containing 50 wt % solids from 43 DE corn syrup and up to 5 wt % organic components was converted to oxygenate intermediates over a deoxygenation catalyst comprising platinum and rhenium loaded on a monoclinic zirconia support. The organic components in the feedstock consisted of 5 wt % acetic acid or 5 wt % furfural. The aqueous stream was fed at WHSV of 3 grams of sugar per gram of catalyst per hour over a packed bed of catalyst. The reactor outlet temperature was set to 265° C.

Figure 6:
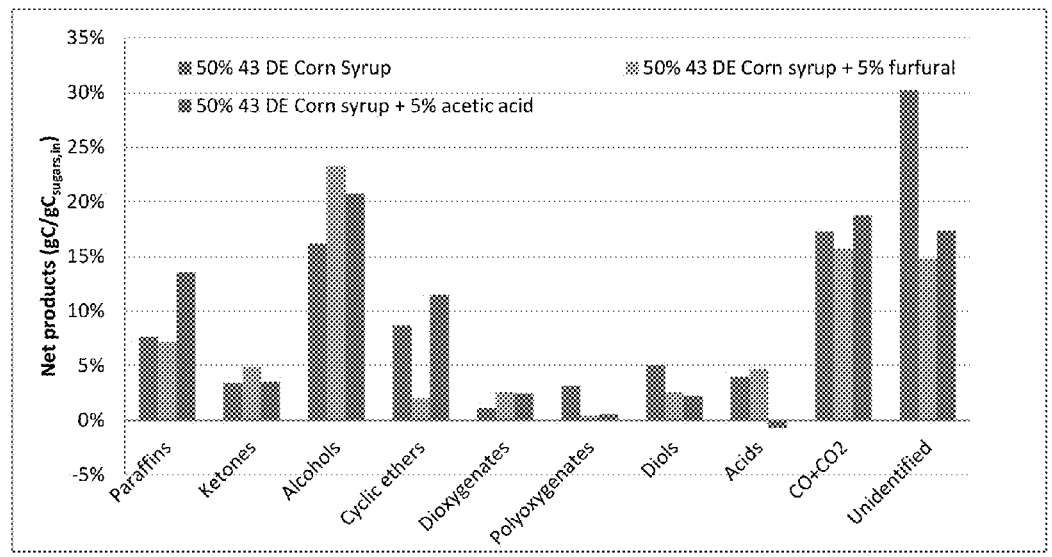
FIG. 6 is an exemplary product distribution illustrating the effect of up to 5 wt % organic components in the feedstock on the product profile for three different feedstocks.

The corn syrup sugars in each of the three feedstocks were completely converted by the process. As shown in FIG. 6, the yield of desirable monooxygenates intermediates (e.g., alcohols and ketones) was improved with acetic acid or furfural present in the feedstock. Low net yields of acids and cyclic ethers indicated that the organic components in the feedstock were partially converted to products by the deoxygenation catalyst.

Example H

An aqueous feedstock containing 40 wt % glucose, 10 wt % xylose, and up to 10 wt % organic components was converted to oxygenate intermediates over a deoxygenation catalyst comprising palladium, molybdenum, and tin loaded on a tungstated-zirconia support. The organic components in the feedstock consisted of 5 wt % furfural or a combination of 5 wt % furfural and 5 wt % acetic acid. The aqueous feedstock was fed at a WHSV of 0.75 grams of sugar per gram of catalyst per hour over a packed bed of catalyst. The reactor outlet temperature was set to 245° C.

Figure 7:
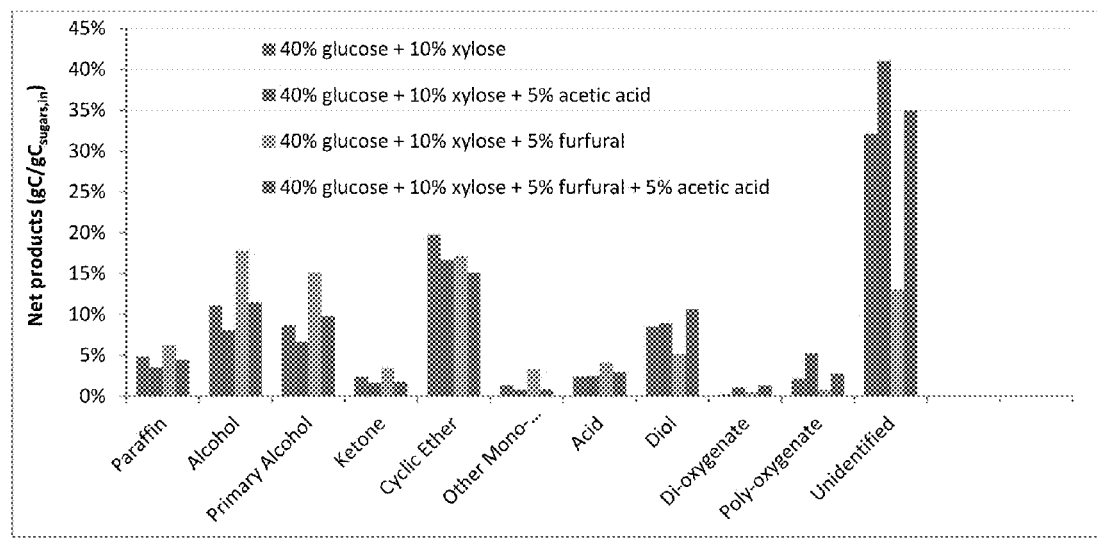
FIG. 7 is an exemplary product distribution illustrating the effect of up to 10 wt % organic components in the feedstock on the product profile for four different feedstocks.

The corn syrup sugars in each of the four feedstocks were completely converted by the process. As shown in FIG. 7, the yield of desirable monooxygenates intermediates (e.g., ketones and alcohols) was improved with furfural present in the feedstock. Up to 5 wt % acetic acid could be added to the feedstock in addition to 5 wt % furfural without significant decrease in alcohol and ketone yields compared to a feedstock free of furfural and acetic acid.

Example I

Figure 8:
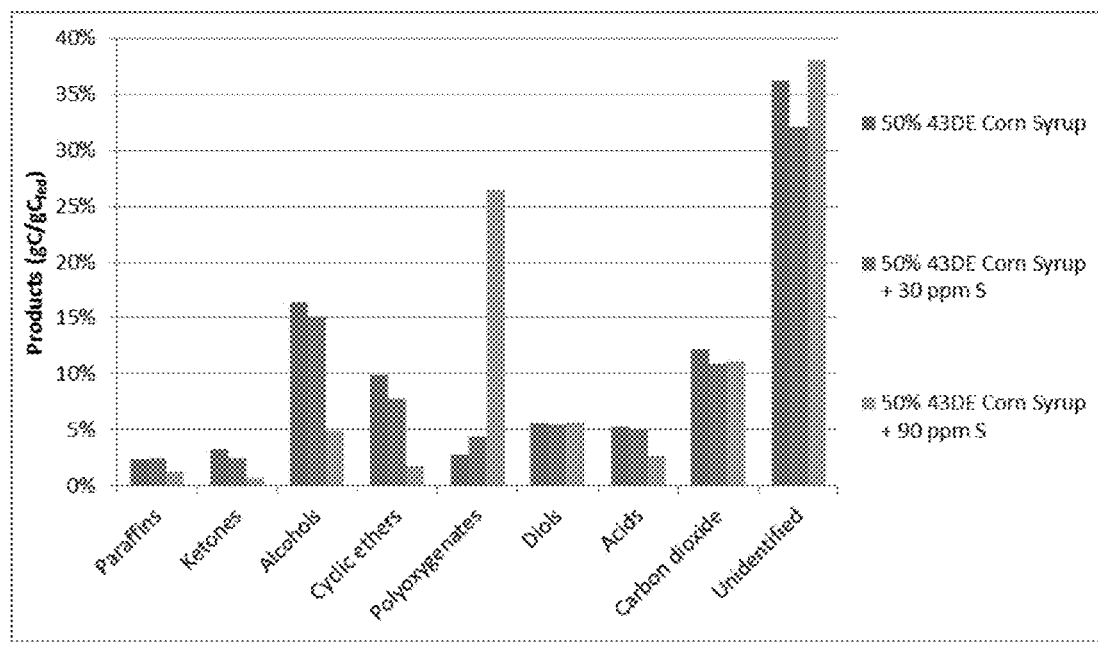
FIG. 8 is an exemplary product distribution illustrating the effect of up to 90 ppm sulfur in the feedstock on the product profile for three different feedstocks.

An aqueous feedstock of 50 wt % DE corn syrup was doped with potassium sulfate to produce a feed with 30-90 ppm sulfur. The feedstock was converted to oxygenate intermediates using a platinum and rhenium catalyst on a monoclinic zirconia support. The reactor conditions included a WHSV of 3 grams of sugar per gram of catalyst per hour and a reactor outlet temperature of 255° C. The corn syrup sugars were completely converted by the process. Product profiles for the three feedstocks are illustrated in FIG. 8.

The feedstock with 30 ppm sulfur produced a similar product to the undoped feedstock, with high yields of oxygenate intermediates (e.g., alcohols and cyclic ethers). The feedstock with 90 ppm sulfur had a high yield of sorbitol (polyoxygenates in FIG. G1), indicating that the presence of sulfur in the feedstock decreased the catalyst activity sufficiently to prevent further conversion of sugar hydrogenation products to desirable monooxygenates.

Example J

Glycerol was used as a model feedstock to facilitate identification of partially deoxygenated oxygenate intermediates. An aqueous feedstock of 50 wt % glycerol was doped with dipotassium phosphate to produce a feedstock with 27 ppm phosphate. The feedstock was converted to oxygenate intermediates using a palladium, molybdenum, tin catalyst on a tungstated-zirconia support. The reactor conditions included a WHSV of 5 grams of glycerol per gram of catalyst per hour and a reactor outlet temperature of 255° C.

Figure 9:
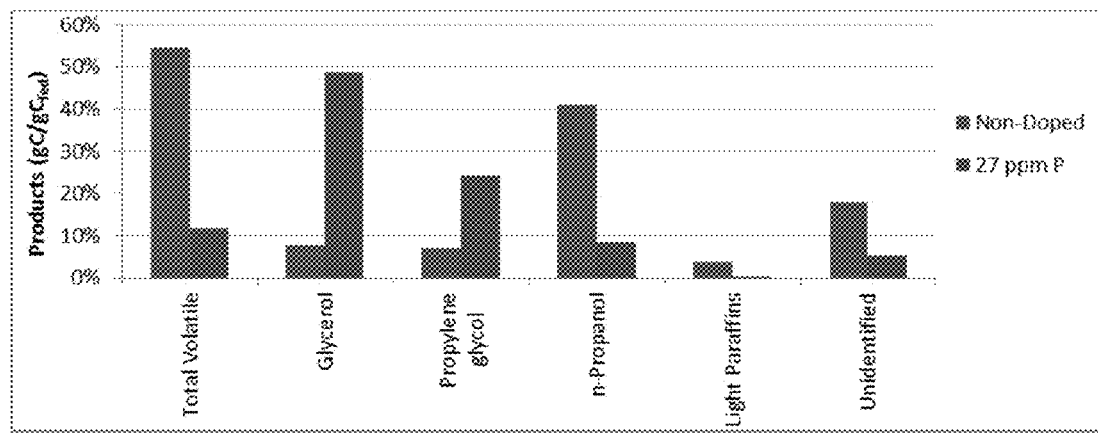
FIG. 9 is an exemplary product distribution illustrating the effect of up to 27 ppm nitrogen in the feedstock on the product profile for two different feedstocks

As shown in FIG. 9 the doped feedstock decreased the catalyst activity, resulting in decreased glycerol conversion and production of desirable monooxygenated intermediates (e.g., n-propanol).

The invention claimed is:
1. A method for producing oxygenated compounds from a biomass-derived feedstock, the method comprising:
  (a) providing an aqueous feedstock, the aqueous feedstock comprising:
    (i) water;

(ii) greater than 20 wt % of a plurality of first oxygenated hydrocarbons, the first oxygenated hydrocarbons selected from the group consisting of monosaccharides, disaccharides, trisaccharides, oligosaccharides, and combinations thereof;

(iii) between 1 wt % and 40 wt % of a plurality of second oxygenated hydrocarbons, the second oxygenated hydrocarbon comprising sugar degradation products; and (iv) ash, wherein the ash comprises less than 75 ppm sulfur and less than 30 ppm phosphorous; and (b) reacting at a temperature of less than 300° C. in a condensed liquid phase reaction or at a temperature of less than 600° C. in a vapor phase reaction a portion of the aqueous feedstock with hydrogen in the presence of a catalyst selected from the group consisting of (i) a first deoxygenation catalyst comprising palladium, molybdenum, and tin on a zirconia support, and (ii) a second catalyst comprising platinum and rhenium on a zirconia support, to produce a reaction product comprising one or more oxygenated compounds selected from the group consisting of an alcohol, a ketone, a cyclic ether, a carboxylic acid, an aldehyde, a diol, and a polyol.

2. The method of claim 1, wherein the aqueous feedstock is prepared by a biomass deconstruction method and the deconstruction method is selected from the group consisting of water hydrolysis, acid hydrolysis, alkaline hydrolysis, organosols pulping, pyrolysis, enzymatic hydrolysis, catalytic biomass deconstruction, and combinations thereof.

3. The method of claim 2, wherein the aqueous feedstock is further prepared by a treatment method and the treatment method is selected from the group consisting of physical separation, chemical separation, neutralization, catalytic reaction, and combinations thereof.

4. The method of claim 1, wherein the aqueous feedstock comprises greater than 30 wt % of the first oxygenated hydrocarbons.

5. The method of claim 1, wherein the aqueous feedstock comprises greater than 5 wt % of the second oxygenated hydrocarbons.

6. The method of claim 1, wherein the aqueous feedstock comprises less than 20 wt % of the second oxygenated hydrocarbons.

7. The method of claim 1, wherein the second oxygenated hydrocarbons comprise less than 15 wt % furfurals.

8. The method of claim 7, wherein the second oxygenated hydrocarbons comprise greater than 5 wt % furfurals.

9. The method of claim 7, wherein the second oxygenated hydrocarbons comprise less than 10 wt % furfurals.

10. The method of claim 1, wherein the ash comprises less than 50 ppm sulfur.

11. The method of claim 1, wherein the ash comprises less than 20 ppm phosphorus.

12. The method of claim 1, wherein the aqueous feedstock further comprises extractives, lignin, lignin derivatives, solids, or combinations thereof.

13. The method of claim 1, further comprising reacting a portion of the reaction product with a condensation catalyst at a condensation temperature and a condensation pressure to produce $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, and a fused aryl.

14. The method of claim 13, wherein the $C_{4+}$ compounds are distilled to provide a composition selected from the group consisting of an aromatic fraction, a gasoline fraction, a kerosene fraction, and a diesel fraction.

15. The method of claim 13, wherein the $C_{4+}$ compounds comprise one or more aryls selected from the group consisting of benzene, toluene, xylene, para-xylene, meta-xylene, and ortho-xylene.

16. A method for producing oxygenated compounds from a biomass-derived feedstock, the method comprising:

(a) deconstructing biomass with a deconstruction method to produce an intermediate feedstock, the intermediate feedstock comprising oxygenated hydrocarbons, ash, extractives, lignin, lignin derivatives, and solids;

(b) treating the intermediate feedstock with a treatment method to produce an aqueous feedstock, the aqueous feedstock comprising:

(i) water;

(ii) greater than 20 wt % of a plurality of first oxygenated hydrocarbons, the first oxygenated hydrocarbons selected from the group consisting of monosaccharides, disaccharides, trisaccharides, oligosaccharides, and combinations thereof;

(iii) between 1 wt % and 40 wt % of a plurality of second oxygenated hydrocarbons, the second oxygenated hydrocarbons comprising sugar degradation products; and (iv) ash, wherein the ash comprises less than 75 ppm sulfur and less than 30 ppm phosphorous; and (c) reacting at a temperature of less than 300° C. in a condensed liquid phase reaction or at a temperature of less than 600° C. in a vapor phase reaction a portion of the aqueous feedstock with hydrogen in the presence of a catalyst selected from the group consisting of (i) a first deoxygenation catalyst comprising palladium, molybdenum, and tin on a zirconia support, and (ii) a second catalyst comprising platinum and rhenium on a zirconia support, to produce one or more oxygenated compounds selected from the group consisting of an alcohol, a ketone, a cyclic ether, a carboxylic acid, an aldehyde, a diol, and a polyol.

17. The method of claim 16, wherein the deconstruction method is selected from the group consisting of water hydrolysis, acid hydrolysis, alkaline hydrolysis, organosolv pulping, pyrolysis, enzymatic hydrolysis, catalytic biomass deconstruction, and combinations thereof.

18. The method of claim 16, wherein the treatment method is selected from the group consisting of physical separation, chemical separation, neutralization, catalytic reaction, and combinations thereof.

19. The method of claim 16, the method further comprising (d) reacting a portion of the oxygenated compounds with a condensation catalyst at a condensation temperature and a condensation pressure to produce $C_{4+}$ compounds selected from the group consisting of a $C_{4+}$ alcohol, a $C_{4+}$ ketone, a $C_{4+}$ alkane, a $C_{4+}$ alkene, a $C_{5+}$ cycloalkane, a $C_{5+}$ cycloalkene, an aryl, and a fused aryl.

20. The method of claim 1, wherein the aqueous feedstock comprises less than 30 wt % of the second oxygenated hydrocarbons.

21. The method of claim 1, wherein the aqueous feedstock comprises less than 35 wt % of the second oxygenated hydrocarbons.

22. The method of claim 1, wherein the aqueous feedstock comprises greater than 40 wt % of the first oxygenated hydrocarbons.

23. The method of claim 1, wherein the aqueous feedstock comprises greater than 50 wt % of the first oxygenated hydrocarbons.

* * * * *